US009763430B2

(12) United States Patent
Gong et al.

(10) Patent No.: US 9,763,430 B2
(45) Date of Patent: Sep. 19, 2017

(54) CHIMERIC GENE CONSTRUCTS FOR GENERATION OF FLUORESCENT TRANSGENIC ORNAMENTAL FISH

(71) Applicants: Zhiyuan Gong, Singapore (SG); Jiangyan He, Cleveland, OH (US); Bensheng Ju, Singapore (SG); Toong Jin Lam, Singapore (SG); Yanfei Xu, Chicago, IL (US); Tie Yan, Singapore (SG)

(72) Inventors: Zhiyuan Gong, Singapore (SG); Jiangyan He, Cleveland, OH (US); Bensheng Ju, Singapore (SG); Toong Jin Lam, Singapore (SG); Yanfei Xu, Chicago, IL (US); Tie Yan, Singapore (SG)

(73) Assignee: National University of Singapore, Singapore (SG)

( * ) Notice: Subject to any disclaimer, the term of this patent is extended or adjusted under 35 U.S.C. 154(b) by 0 days.

(21) Appl. No.: 13/738,704

(22) Filed: Jan. 10, 2013

(65) Prior Publication Data

US 2014/0007265 A1 Jan. 2, 2014

Related U.S. Application Data

(60) Continuation of application No. 13/334,444, filed on Dec. 22, 2011, now Pat. No. 8,378,169, which is a continuation of application No. 11/749,032, filed on May 15, 2007, now Pat. No. 8,153,858, which is a continuation of application No. 10/605,708, filed on Oct. 21, 2003, now Pat. No. 7,834,239, which is a division of application No. 09/913,898, filed as application No. PCT/SG99/00079 on Jul. 16, 1999, now Pat. No. 7,135,613.

(30) Foreign Application Priority Data

Feb. 18, 1999 (SG) .................................. 9900811-2

(51) Int. Cl.

*A01K 67/027* (2006.01)
*C07K 14/435* (2006.01)
*C12N 15/85* (2006.01)
*G01N 33/74* (2006.01)

(52) U.S. Cl.

CPC .... *A01K 67/0275* (2013.01); *C07K 14/43595* (2013.01); *C12N 15/85* (2013.01); *C12N 15/8509* (2013.01); *G01N 33/743* (2013.01); *A01K 2217/05* (2013.01); *A01K 2217/20* (2013.01); *A01K 2227/40* (2013.01); *A01K 2267/02* (2013.01); *A01K 2267/0393* (2013.01); *C12N 2830/00* (2013.01); *C12N 2830/008* (2013.01); *C12N 2830/42* (2013.01); *C12N 2830/80* (2013.01); *C12N 2840/20* (2013.01)

(58) Field of Classification Search

CPC .................................................. A01K 67/0275

See application file for complete search history.

(56) References Cited

U.S. PATENT DOCUMENTS

| | | | | |
|---|---|---|---|---|
| 5,028,839 | A | 7/1991 | Abeywickrama et al. | 313/487 |
| 5,876,995 | A | 3/1999 | Bryan | 435/189 |
| 5,998,698 | A | 12/1999 | Cooper et al. | 800/20 |
| 6,113,886 | A | 9/2000 | Bryan | 424/49 |
| 6,152,358 | A | 11/2000 | Bryan | 435/189 |
| 6,232,107 | B1 | 5/2001 | Bryan et al. | 435/189 |
| 6,247,995 | B1 | 6/2001 | Bryan | 446/473 |
| 6,307,121 | B1 | 10/2001 | Winn et al. | 800/3 |
| 6,380,458 | B1 | 4/2002 | Lin | 800/20 |
| 6,436,682 | B1 | 8/2002 | Bryan et al. | 435/189 |
| 6,472,583 | B1 | 10/2002 | Winn | 800/3 |
| 2002/0013955 | A1 | 1/2002 | Ogden et al. | 800/20 |
| 2002/0178461 | A1 | 11/2002 | Lin | 800/20 |

FOREIGN PATENT DOCUMENTS

| | | |
|---|---|---|
| WO | WO 96/03034 | 2/1996 |
| WO | WO 98/15627 | 4/1998 |
| WO | WO 98/56902 | 12/1998 |

OTHER PUBLICATIONS

"FDA Fish Classification Guide", Center for Veterinary Medicine Program Policy and Procedure Manual Guide 1240.4260, Oct. 29, 1997.

Amsterdam et al., "Requirements for green fluorescent protein detection in transgenic zebrafish embryos," *Gene*, 173:99-103, 1996.

Amsterdam et al., "The aequorea victoria Green fluorescent protein can be used as a reporter in live zebrafish embryos," *Developmental Biology*, 171:123-129, 1995.

Amsterdam et al., "Transient and transgenic expression of green fluorescent protein (GFP) in living zebrafish embryos," *CLONETECHniques*, Jul. 1995.

Argenton et al., "An activation domain of the helix-loop-helix transcription factor E2A shows cell type preference in vivo in microinjected zebra fish embryos," *Mol. Cell. Biol.*, 16:1714-1721, 1996.

Barro et al., "Induction of a secondary axis in zebrafish by evei gene overexpression," p. 37, *Abstracts of papers presented at the 1994 meeting on Zebrafish Development & Genetics*, Apr. 27-May 1, 1994.

Bartley et al., "The use of inter-specific hybrids in aquaculture and fisheries," *Reviews in Fish Biology and Fisheries*, 10:325-337, 2001.

(Continued)

*Primary Examiner* — Valarie Bertoglio

(74) *Attorney, Agent, or Firm* — Parker Highlander PLLC

(57) ABSTRACT

Four zebrafish gene promoters, which are skin specific, muscle specific, skeletal muscle specific and ubiquitously expressed respectively, were isolated and ligated to the 5' end of the EGFP gene. When the resulting chimeric gene constructs were introduced into zebrafish, the transgenic zebrafish emit green fluorescence under a blue light or ultraviolet light according to the specificity of the promoters used. Thus, new varieties of ornamental fish of different fluorescence patterns, e.g., skin fluorescence, muscle fluorescence, skeletal muscle-specific and/or ubiquitous fluorescence, are developed.

7 Claims, 15 Drawing Sheets

(56) References Cited

OTHER PUBLICATIONS

Bayer and Campos-Ortega, "A transgene containing lacZ is expressed in primary sensory neurons in zebrafish," *Development*, 115:421-426, 1992.
Bayer et al., "Functional test of the ependymin promoter by transient expression in zebrafish embryos," The Zebrafish Science Monitor, p. 3, Jun. 1, 1992.
Bearzotti et al., "Gene expression following transfection of fish cells," *J. Biotechnol.*, 26:315-325, 1992.
Betancourt et al., "Efficiency of introns from various origins in fish cells," *Mol. Mar. Biol. Biotechnol.*, 2:181-188, 1993.
Brem et al., "Gene transfer in tilapia ( *Oreochromis niloticus*)," *Aquaculture*, 68:209-219, 1988.
Chalife et al., "Green fluorescent protein as a marker for gene expression," *Science*, 263:802-805, 1994.
Chen and Fishman, "Tinman in zebrafish heart development," p. 135, *Abstracts of papers presented at the 1994 meeting on Zebrafish Development & Genetics*, Apr. 27-May 1, 1994.
Chen et al., "Enhanced viral resistance in transgenic mice expressing the human beta 1 interferon," *J. of Virology*, 62:3883-3887, 1988.
Chen et al., "Isolation and characterization of Tilapia ( *Oreochromis mossambicus*) insulin-like growth factors gene and proximal promoter region," *DNA and Cell Biology*, 17:359-376, 1998.
Chen et al., "Isolation of a skeletal muscle specific myosin light chain gene promoter from zebrafish by an improved linker mediated PCR," p. 134, *Abstracts of papers presented at the 1994 meeting on Zebrafish Development & Genetics*, Apr. 27-May 1, 1994.
Chourrout et al., "High efficiency gene transfer in rainbow trout (salmo gairdneri rich.) by microinjection into egg cytoplasm," Aquaculture, 51:143-150, 1986.
Codey-Smith et al., "Production of haploid and diploid androgenotes—genetic implications and utilities," p. 93, *Abstracts of papers presented at the 1994 meeting on Zebrafish Development & Genetics*, Apr. 27-May 1, 1994.
Cormack et al., "FAC optimized mutants of the green fluorescent protein (GFP)," *Gene*, 173:33-38, 1996.
Cozzi and White, "The generation of transgenic pigs as potential organ donors for humans," *Nature Medicine*, 1:964-966, 1995.
Culp et al., "High-frequency germ-line transmission of plasmid DNA sequences injected into fertilized zebrafish eggs," *PNAS*, 88:7953-7957, 1991.
Devlin et al., "Extraordinary salmon growth," *Nature*, 371:209-210, 1994.
Devlin et al., "Production of germline transgenic Pacific salmonids with dramatically increased grrowth performance," *Can. J. Fish. Aquat. Sci.*, 52:1376-1384, 1995.
Dialog Search Report, pp. 1-10, Dec. 3, 2002.
Dialog Search Report, pp. 1-15, Nov. 21, 2002.
Dialog Search Report, pp. 1-16, Nov. 15, 2002.
Dialog Search Report, pp. 1-3, Nov. 21, 2002.
Dialog Search Report, pp. 1-32, Nov. 21, 2002.
Dialog Search Report, pp. 1-4, Nov. 21, 2002.
Dialog Search Report, pp. 1-43, Dec. 3, 2002.
Du et al., "Growth enhancement in transgenic Atlantic salmon by the use of an 'all fish' chimeric growth hormone gene construct," *Bio/Technology*, 10:176-181, 1992.
Du et al., "Melanocyte formation in zebrafish embryos is perturbed by ectopic expression of dorsalin-1 in the notochord," p. 58, *Abstracts of papers presented at the 1994 meeting on Zebrafish Development & Genetics*, Apr. 27-May 1, 1994.
Fahrenkrug et al., "Dicistronic gene expression in developing zebrafish," *Mar. Biotechnol.*, 1:552-561, 1999.
Flanagan and Wagner, "A bi-functional reporter plasmid for the simultaneous transient expression assay of two herpes simplex virus promoters" *Virus Genes*, 1(1):61-71, 1987.
Gibbs et al., "An in vivo screen for the luciferase transgene in zebrafish," *Molecular Marine Biology and Biotechnology*, 3:307-316, 1994.
Gilland et al., "Imaging of multicellular large-scale rhythmic calcium waves during zebrafish gastrulation," *Proc. Natl. Acad. Sci.*, USA, 96:157-161, 1999.
Gomez-Chiarri et al., "Introduction of foreign genes into the tissue of live fish by direct injection and particle bombardment," *Diseases of Aquatic Organisms*, 27:5-21, 1996.
Gong et al., "Development of transgenic fish for ornamental and bioreactor by strong expression of fluorescent proteins in the skeletal muscle," *Biochem. Biophys. Res. Commun.*, 308(1):58-63, 2003.
Gong et al., "Rapid identification and isolation of zebrafish cDNA clones," *Gene*, 201:87-98, 1997.
Gong et al., "Tissue distribution of fish antifreeze protein mRNAs," *Can. J. Zool.*, 70:810-814, 1992.
Gong, "Trangenic fluorescent fish," *Asia-Pacific Biotech News*, 2(16):280, 1998.
Gordon et al., "Genetic transformation of mouse embryos by microinjection of purified DNA," *Proc. Natl. Acad. Sci.*, USA, 77:7380-7384, 1980.
Gross et al., "Molecular analysis and growth evaluation of northern pike ( *Esox lucius*) microinjected with growth hormone genes," *Aquaculture*, 103:253-273, 1992.
Hackett et al, The Molecular Genetics of Transgenic Fish, "*Recent Advances in Marine Biotechnology* ", 4:77-145, 2000.
Hackett, "The molecular biology of transgenic fish," *Biochemistry and Molecular Biology of Fishes*, 2(Chapter 9):207-240, 1993.
Hernandez et al., "Characterization of transgenic tilapia lines with different ectopic expression of tilapia growth hormone," *Mol. Mar. Biol. Biotechnol.*, 6(4):364-375, 1997.
Higashijima et al., "High-frequency generation of transgenic zebrafish which reliably express GFP in whole muscles or the whole body by using promoters of zebrafish origin," *Developmental Biology*, 192:289-299, 1997.
Hua, Chan Chiew, "Isolation of Myosin Light Chain Promoter using Linker-Mediated PCR," thesis submitted in partial fulfillment for the degree of Bachelor of Science with Honours in Cell and Molecular Biology, Departments of Botany & Zoology, National University of Singapore, 1995/1996.
Hugo, M., *The Goldfish and Its Systematic Culture With a View of Profit*. McDonald & Eick, Print: Cincinnati. 1883.
Joore et al., "Regulation of the zebrafish goosecoid promoter by mesoderm inducing factors and Xwnt1," *Mechanisms of Development*, 55:3-18, 1996.
Ju et al., "Faithful expression of green fluorescent protein (gfp) in transgenic zebrafish embryos under control of zebrafish gene promoters," *Developmental Genetics*, 25:158-167, 1999.
Kermekchiev et al., "Every enhancer works with every promoter for all the combinations tested: could new regulatory pathways evolve by enhancer shuffling?" *Gene Expression*, 1:71-81, 1991.
Khoo et al., "Sperm cells as vectors for introducing foreign DNA into zebrafish," *Aquaculture*, 107:1-19, 1992.
Kim et al., "Neuron-specific expression of a chicken gicerin cDNAin transient transgenic zebrafish," *Neurochemical Research*, 21:231-237, 1996.
Kuo et al., "Determination of a necdin cis-acting element required for neuron specific expression by using zebra fish," *Biochem. Biophys. Res. Commun.*, 211:438-446, 1995.
Lathe and Mullins, "Transgenic animals as models for human disease—report of an EC study group," *Transgenic Research*, 2:286-299, 1993.
Lian, Tian Ho "Functional Analysis of a Skeletal Muscle-Specific Promoter in Zebrafish," thesis submitted to the School of Biological Sciences, National University of Singapore, 1996/1997.
Liao et al., "An alternative linker-mediated polymerase chain reaction method using a dideoxynucleotide to reduce amplification background," *Analytical Biochemistry*, 253:137-139, 1997.
Lin et al., "lacZ expression in germline transgenic zebrafish can be detected in living embryos," *Developmental Biology*, 161:77-83, 1994.
Lin, "Methods in Molecular Biology," Chapter 36 in Developmental Biology Protocols, vol. II, *Tuan and Lo Humana Press Inc.*, 136:375-383, 2000.

(56) References Cited

OTHER PUBLICATIONS

Liu et al., "Development of expression vectors for transgenic fish," *Bio/Technology*, 8:1268-1272, 1990.
Living Colors Subcellular Localization Vectors, CLONTECHniques XIII, 4:8-9, 1998.
Long et al., "GATA-1 expression pattern can be recapitulated in living transgenic zebrafish using GFP reporter gene," *Development*, 124:4105-4111, 1997.
Lythgoe et al., "Changes in spectral reflexions from the iridophores of the neon tetra," *J. Physiol.*, 325:23-34, 1982.
Maga and Murray, "Mammary gland expression of transgenes and the potential for altering the properties of milk," *Bio/Technology*, 13:1452-1457, 1995.
Malicki et al., "Genetic analysis of early ear development in zebrafish," p. 59, *Abstracts of papers presented at the 1994 meeting on Zebrafish Development & Genetics*, Apr. 27-May 1, 1994.
Meng et al., "Promoter analysis in living zebrafish embryos identifies a cis-acting motif required for neuronal expression of GATA-2," *Proc. Natl. Acad. Sci.*, USA, 94:6267-6272, 1997.
Moss et al., "Green fluorescent protein marks skeletal muscle in murine cell lines and zebrafish," *Gene*, 173:89-98, 1996.
Muller et al., "Activator effect on coinjected enhancers on the muscle-specific expression of promoters in zebrafish embryos," *Mol. Reprod. and Develop.*, 47:404-412, 1997.
Muller et al., "Tissue specific activator effect of enhancers on the expression of minimal promoters in coinjected zebrafish embryos provides a rapid enhancer assay," p. 92, *Abstracts of papers presented at the 1994 meeting on Zebrafish Development & Genetics*, Apr. 27-May 1, 1994.
Office Communication issued in U.S. Appl. No. 13/334,444, dated Oct. 11, 2012.
Office Communication issued in U.S. Appl. No. 13/334,444, dated May 25, 2012.
Office Communication issued in U.S. Appl. No. 11/749,032, dated Sep. 26, 2011.
Office Communication issued in U.S. Appl. No. 11/749,032, dated Jul. 5, 2011.
Office Communication issued in U.S. Appl. No. 11/749,032, dated Apr. 18, 2011.
Office Communication issued in U.S. Appl. No. 11/749,032, dated Dec. 1, 2010.
Office Communication issued in U.S. Appl. No. 11/749,032, dated Dec. 10, 2009.
Office Communication issued in U.S. Appl. No. 11/749,032, dated Jun. 10, 2009.
Office Communication issued in U.S. Appl. No. 11/749,032, dated Dec. 10, 2008.
Office Communication issued in U.S. Appl. No. 11/749,032, dated Sep. 30, 2008.
Office Communication issued in U.S. Appl. No. 10/605,708, dated Mar. 10, 2010.
Office Communication issued in U.S. Appl. No. 10/605,708, dated Nov. 30, 2009.
Office Communication issued in U.S. Appl. No. 10/605,708, dated Jan. 29, 2009.
Office Communication issued in U.S. Appl. No. 10/605,708, dated Jun. 10, 2008.
Office Communication issued in U.S. Appl. No. 10/605,708, dated Jul. 9, 2007.
Office Communication issued in U.S. Appl. No. 10/605,708, dated May 10, 2007.
Office Communication issued in U.S. Appl. No. 10/605,708, dated Nov. 3, 2006.
Office Communication issued in U.S. Appl. No. 10/605,708, dated Mar. 8, 2006.
Office Communication issued in U.S. Appl. No. 10/605,708, dated Dec. 14, 2005.
Office Communication issued in U.S. Appl. No. 09/913,898, dated Jun. 17, 2005.
Office Communication issued in U.S. Appl. No. 09/913,898, dated Nov. 17, 2004.
Office Communication issued in U.S. Appl. No. 09/913,898, dated Oct. 5, 2004.
Office Communication issued in U.S. Appl. No. 09/913,898, dated Dec. 18, 2003.
Office Communication issued in U.S. Appl. No. 09/913,898, dated Dec. 21, 2005.
Okabe et al., "'Green mice' as a source of ubiquitous green cells," *FEBS Letter*, 407(3):313-319, 1997.
Olson et al., "Regulation of muscle differentiation by the MEF2 family of MADS box transcription factors," *Developmental Biology*, 172:2-14, 1995.
Palmiter et al., "Dramatic growth of mice that develop from eggs microinjected with metallothionein-growth hormone fusion genes," *Nature*, 300:611-615, 1982.
PCT International Search Report issued in International Patent Application No. PCT/SG99/00079, dated Dec. 13, 1999.
Penman et al., "Factors affecting survival and integration following microinjection of novel DNA into rainbow trout eggs," *Aquaculture*, 85:35-50, 1990.
Powers et al., "Electroporation: a method for transferring genes into the gametes of zebrafish ( *Brachydanio rerio*), channel catfish ( *Ictalurus punctatus*), and common carp ( *Cyprinus carpio*)," *Mol. Marine Biol. and Biotech.*, 1(4/5):301-308, 1992.
Prasher et al., "Primary structure of the Aequorea victoria green-fluorescent protein," *Gene*, 111:229-233, 1992.
Rinder et al., "Molecular analysis of the ependymin gene functional test of its promoter region by transient expression in Brachydanio rerio," *DNA and Cell Biology*, 11:425-432, 1992.
Rossant and Hopkins, "O fin and fur: mutational analysis of vertebrate embryonic development," *Genes & Development*, 6:1-13, 1992.
Sambrook et al., (eds.), *Molecular Cloning, a Laboratory Manual*, 2nd edition, pp. 9.14-9.23, 1989.
Schwarz et al., "Transcription factors controlling muscle-specific gene expression," In: *Gene Expression: General and Cell-type-specific*, Karin (ed.), Chapter 5: 93-115, Boston : Birkhäuser, c1993.
Seah, "Making zebra fish that glow in the dark," in the Straits Times, Monday, Aug. 10, 1998.
Sin et al., "Gene transfer in chinook salmon ( *Oncorhynchus tshawytscha*) by electroporating sperm in the presence of pRSV-lacZ DNA," Aquaculutre, 117:57-69, 1993.
Spaniol et al., "Using homoogous sequences to produce transgenic zebrafish," p. 208, *Abstracts of papers presented at the 1994 meeting on Zebrafish Development & Genetics*, Apr. 27-May 1, 1994.
Stachel et al., "Molecular analysis of the zebrafish goosecond promoter," p. 36, *Abstracts of papers presented at the 1994 meeting on Zebrafish Development & Genetics*, Apr. 27-May 1, 1994.
Stuart et al., "Replication, integration and stable germ-line transmission of foreign sequences injected into early zebrafish embryos," *Development*, 103:403-412, 1988.
Stuart et al., "Stable lines of transgenic zebrafish exhibit reproducilbe patterns of transgene expression," *Development*, 109:577-584, 1990.
Szelei et al., "Liposome-mediated gene transfer in fish embryos," *Transgenic Research*, 3:116-119, 1994.
Takeuchi et a, "Green fluorescent protein as a cell-labeling tool and a reporter of gene expression in transgenic rainbow trout," *Mar. Biotechnol.*, 1:448-457, 1999.
Talbot et al., "Towards a molecular analysis of cyclops," p. 209, *Abstracts of papers presented at the 1994 meeting on Zebrafish Development & Genetics*, Apr. 27-May 1, 1994.
Thisse et al., "Structure of the zebrafish snail1 gene and its expression in wild-type, spadetail and no tail mutant embryos," *Development*, 119:1203-1215, 1993.
Tsai et al., "Electroporation of sperm to introduce foreign DNA into the genome of loach ( *Misgurnus anguillicaudatus*)," *Can. J. Fish. Aquat. Sci.*, 52:776-787, 1995.
Wakamatsu et al., "The see-through medaka: a fish model that is transparent throughout life," *Proc. Natl. Acad. Sci.*, USA, 98:10046-10050, 2001.

(56) References Cited

OTHER PUBLICATIONS

Wang and Hazelrigg, "Implications for bcd mRNA localization from spatial distribution of exu protein in *Drosophila oogenesis*," *Nature*, 369:400-402, 1994.
Wang et al., "Expression of the antifreeze protein gene in transgenic goldfish ( *Carassius auratus*) and its implication in cold adaption," *Mol. Marine Biol. and Biotechnology*, 4:20-26, 1995.
Wee, "Quantum Nanostructures," in the National University of Singapore Faculty Science Research Newletter, 2(4):1-2, Oct. 1998.
Westerfield et al., "Specific activation of mammalian Hox promoters in mosaic transgenic zebrafish," *Genes & Development*, 6:591-598, 1992.
Wright et al., "High level expression of active human alpha-1-antitrypsin in the milk of transgenic sheep," *Bio/Technology*, 9:830-834, 1991.
Xu et al., "Fast skeletal muscle-specific expression of a zebrafish myosin light chain 2 gene and characterization of its promoter by direct injection into skeletal muscle," *DNA and Cell Biology*, 18:85-95, 1999.
Yang et al., "Optimized codon usage and chromophore mutations provide enhanced sensitivity with the green fluorescent protein," *Nucleic Acids Research*, 24:4592-4593, 1996.
Yang et al., "Improved fluorescence and dual color detection with enhanced blue and green variants of the green fluorescent protein," *J. Biol. Chem.*, 273(14): 8212-8216, 1998.
Yanong et al., "Reproductive management of freshwater ornamental fish," *Seminars in Avian and Exotic Pet Medicine*, 5(4):222-235, 1996.
Yue et al., "Fusion expression of green fluorescent protein and HCV capsid antigene in *Escherichia coli* cells," *Chin. J. Biotechnology*, 13(4):239-246, 1997. (Abstract).
Zelenin et al., "The delivery of foreign genes into fertilized fish eggs using high-velocity microprojectiles," *FEBS Letters*, 287:118-120, 1991.
Zhu et al., "Novel gene transfer into the fertilized eggs of gold fish ( *Carassius auratus* L. 1758)," *Journal of applied ichthyology*, 1:31-34, 1985.

| Exp. in skeletal muscles (%) | Levels of Exp. in Skeletal muscles (%) | | |
|---|---|---|---|
| | S | M | W |
| 100 | 23 | 37 | 40 |
| 100 | 14 | 23 | 63 |
| 100 | 2 | 30 | 68 |
| 100 | 0 | 15 | 85 |
| 95.7 | 0 | 11 | 89 |
| 46.6 | 0 | 0 | 100 |

S, Strong Expression; M, Medial Expression; W, Weak Expression

```
                              SEQUENCE LISTING

<160> NUMBER OF SEQ ID NOS: 24

<210> SEQ ID NO 1
<211> LENGTH: 2480
<212> TYPE: DNA
<213> ORGANISM: Danio rerio
<220> FEATURE:
<221> NAME/KEY: CDS
<222> LOCATION: (90)..(1586)
<220> FEATURE:
<221> NAME/KEY: primer bind
<222> LOCATION: (66)..(85)
<223> OTHER INFORMATION: CK2
<220> FEATURE:
<221> NAME/KEY: primer bind
<222> LOCATION: (97)..(120)
<223> OTHER INFORMATION: CK1
<220> FEATURE:
<221> NAME/KEY: polyA signal
<222> LOCATION: (24467..(2451)

<400> SEQUENCE: 1

ctctcctttg tgagcaacct cctccactca ctcctctctc agagagcact ctcgtacctc      60

cttctcagca actcaaagac acaggcatc atg tca acc agg tct atc tct tac      113
                                Met Ser Thr Arg Ser Ile Ser Tyr
                                1               5

tcc agc ggt ggc tcc atc agg agg ggc tac acc agc cag tca gcc tat      161
Ser Ser Gly Gly Ser Ile Arg Arg Gly Tyr Thr Ser Gln Ser Ala Tyr
    10                  15                  20

gca gta cct gcc ggc tct acc agg atg agc tca gtg acc agt gtc agg      209
Ala Val Pro Ala Gly Ser Thr Arg Met Ser Ser Val Thr Ser Val Arg
25                  30                  35                  40

aga tct ggt gtg ggt gcc agc cca ggc ttc ggt gcc ggt ggc agc tac      257
Arg Ser Gly Val Gly Ala Ser Pro Gly Phe Gly Ala Gly Gly Ser Tyr
                45                  50                  55

agc ttt agc agc agc agc atg ggt gga ggc tat gga agt ggt ctt ggt      305
Ser Phe Ser Ser Ser Ser Met Gly Gly Gly Tyr Gly Ser Gly Leu Gly
            60                  65                  70

gga ggt ctc ggt ggg ggc atg ggc ttt cgt tgc ggg ctt cct atc aca      353
Gly Gly Leu Gly Gly Gly Met Gly Phe Arg Cys Gly Leu Pro Ile Thr
        75                  80                  85

gct gta act gtc aac cag aac ctg ttg gcc ccc tta aac ctg gaa atc      401
Ala Val Thr Val Asn Gln Asn Leu Leu Ala Pro Leu Asn Leu Glu Ile
```

-continued

```
     90                  95                  100

gac ccc aca att caa gct gtc cgc act tca gag aaa gag cag att aag      449
Asp Pro Thr Ile Gln Ala Val Arg Thr Ser Glu Lys Glu Gln Ile Lys
105                 110                 115                 120

acc ttc aac aac cgc ttc gct ttc ctc atc gac aaa gtg cgc ttc ctg      497
Thr Phe Asn Asn Arg Phe Ala Phe Leu Ile Asp Lys Val Arg Phe Leu
                125                 130                 135

gaa cag cag aac aag atg ctt gag acc aaa tgg agt ctt ctc caa gaa      545
Glu Gln Gln Asn Lys Met Leu Glu Thr Lys Trp Ser Leu Leu Gln Glu
            140                 145                 150

cag aca acc aca cgt tcc aac atc gat gcc atg ttt gag gca tac atc      593
Gln Thr Thr Thr Arg Ser Asn Ile Asp Ala Met Phe Glu Ala Tyr Ile
        155                 160                 165

tct aac ctg cgc aga cag ctc gat gga ctg gga aat gag aag atg aag      641
Ser Asn Leu Arg Arg Gln Leu Asp Gly Leu Gly Asn Glu Lys Met Lys
    170                 175                 180

ctg gag gga gag ctg aag aac atg cag ggc ctg gtt gag gac ttc aag      689
Leu Glu Gly Glu Leu Lys Asn Met Gln Gly Leu Val Glu Asp Phe Lys
185                 190                 195                 200

aac aag tac gag gat gag atc aac aag cgt gct tcc gta gag aat gag      737
Asn Lys Tyr Glu Asp Glu Ile Asn Lys Arg Ala Ser Val Glu Asn Glu
                205                 210                 215

ttt gtc ctg ctc aag aag gat gtt gat gca gcc tac atg aac aag gtt      785
Phe Val Leu Leu Lys Lys Asp Val Asp Ala Ala Tyr Met Asn Lys Val
            220                 225                 230

gag ctt gaa gcc aag gtt gat gct ctt cag gat gag atc aac ttc ctc      833
Glu Leu Glu Ala Lys Val Asp Ala Leu Gln Asp Glu Ile Asn Phe Leu
        235                 240                 245

agg gca gtc tac gag gct gaa ctc cgg gag ctc cag tct cag atc aag      881
Arg Ala Val Tyr Glu Ala Glu Leu Arg Glu Leu Gln Ser Gln Ile Lys
    250                 255                 260

gac aca tct gtt gtt gta gaa atg gac aac agc aga aac ctg gat atg      929
Asp Thr Ser Val Val Val Glu Met Asp Asn Ser Arg Asn Leu Asp Met
265                 270                 275                 280

gac tcc atc gtg gct gaa gtt cgc gct cag tat gaa gac atc gcc aac      977
Asp Ser Ile Val Ala Glu Val Arg Ala Gln Tyr Glu Asp Ile Ala Asn
                285                 290                 295

cgc agc cgt gcc gag gca gag agc tgg tac aaa cag aag ttt gag gag     1025
Arg Ser Arg Ala Glu Ala Glu Ser Trp Tyr Lys Gln Lys Phe Glu Glu
            300                 305                 310

atg cag agc acc gct ggt cag tat ggt gat gac ctc cgc tca aca aag     1073
Met Gln Ser Thr Ala Gly Gln Tyr Gly Asp Asp Leu Arg Ser Thr Lys
        315                 320                 325

gct gag att gct gaa ctc aac cgc atg atc gcc cgc ctg cag aac gag     1121
Ala Glu Ile Ala Glu Leu Asn Arg Met Ile Ala Arg Leu Gln Asn Glu
    330                 335                 340

atc gat gct gtc aag gca cag cgt gcc aac ttg gag gct cag att gct     1169
Ile Asp Ala Val Lys Ala Gln Arg Ala Asn Leu Glu Ala Gln Ile Ala
345                 350                 355                 360

gag gct gaa gag cgt gga gag ctg gca gtg aag gat gcc aag ctc cgc     1217
Glu Ala Glu Glu Arg Gly Glu Leu Ala Val Lys Asp Ala Lys Leu Arg
                365                 370                 375

atc agg gag ctg gag gaa gct ctt cag agg gcc aag caa gac atg gcc     1265
Ile Arg Glu Leu Glu Glu Ala Leu Gln Arg Ala Lys Gln Asp Met Ala
            380                 385                 390

cgc cag gtc cgc gag tac cag gag ctc atg aac gtc aaa ttg gct ctg     1313
Arg Gln Val Arg Glu Tyr Gln Glu Leu Met Asn Val Lys Leu Ala Leu
        395                 400                 405

gac att gag atc gcc acc tac agg aaa ctg ttg gaa gga gag gag agc     1361
```

-continued

```
Asp Ile Glu Ile Ala Thr Tyr Arg Lys Leu Leu Glu Gly Glu Glu Ser
    410                 415                 420

aga ctg tcc agc ggt gga gct caa gct acc att cat gtt cag cag acc     1409
Arg Leu Ser Ser Gly Gly Ala Gln Ala Thr Ile His Val Gln Gln Thr
425                 430                 435                 440

tcc gga ggt gtt tca tct ggt tat ggt ggt agc ggc tct ggt ttc ggc     1457
Ser Gly Gly Val Ser Ser Gly Tyr Gly Gly Ser Gly Ser Gly Phe Gly
                445                 450                 455

tac agc agt ggc ttc agc agt ggt ggg tca gga tac ggt agt gga tca     1505
Tyr Ser Ser Gly Phe Ser Ser Gly Gly Ser Gly Tyr Gly Ser Gly Ser
            460                 465                 470

gga ttc ggt tct gga tca ggg tat ggt gga ggc tcc atc agc aaa acc     1553
Gly Phe Gly Ser Gly Ser Gly Tyr Gly Gly Gly Ser Ile Ser Lys Thr
        475                 480                 485

agt gtc acc acc gtc agc agt aaa cgc tat taa ggagaagccc gcccaaaccc   1606
Ser Val Thr Thr Val Ser Ser Lys Arg Tyr
    490                 495

ccagccgaca cagtttccaa ccttccttac ctgcaactag atcccttctg aaccttctta   1666

cgactcaaac catctatggt gctatatttt agccagacag ctgtcccctg ttaatgagga   1726

gatgtggacg atgattttta aagtacaaaa taagttttag attgttctgt gtgttgatgg   1786

tagttacccg tatcatgcat ctcctgtctg gtggtgtcac tgccatttta aatcatcaac   1846

ccaactacac taaaacgata ccaggaagaa tcgtgctcca agccactgaa tagtcttatt   1906

tctgcactga tatgtacagg gaaagtgaga cacatagaaa ccactgtaac ctacgtagta   1966

ctatggtttc actggatcag ggtgtgctta tacaagttcc tgaatgtctt gtttgaatgt   2026

tttgtgctgt tacaagctcc ctgctgtagt tttgctgact aatctgactt ttgtcatttt   2086

gctatggctg tcagagttgg tttacctatt ttctataaaa tgtatatggc agtcagccaa   2146

taactgatga caattgcttg tgggctacta atgtccagtt acctcacatt caagggagat   2206

ctgttacagc aaaaaacagg cacaatggga tttatgtgga ccatccctcc ttaaccttgt   2266

gtactttccg tgttggaagt ggtgactgta ctgccttaca cattcccctg tattcaactg   2326

gcttccagag catattttac atccccggtt ataaatggaa aatgcaagaa aactgaaaca   2386

atgttcaacc agatttattt ggtattgatt gacgagacac caacttgaaa tttgaataca   2446

ataaatctga gaccacaaaa aaaaaaaaaa aaaa                               2480


<210> SEQ ID NO 2
<211> LENGTH: 498
<212> TYPE: PRT
<213> ORGANISM: Danio rerio

<400> SEQUENCE: 2

Met Ser Thr Arg Ser Ile Ser Tyr Ser Ser Gly Gly Ser Ile Arg Arg
  1               5                  10                  15

Gly Tyr Thr Ser Gln Ser Ala Tyr Ala Val Pro Ala Gly Ser Thr Arg
            20                  25                  30

Met Ser Ser Val Thr Ser Val Arg Arg Ser Gly Val Gly Ala Ser Pro
        35                  40                  45

Gly Phe Gly Ala Gly Gly Ser Tyr Ser Phe Ser Ser Ser Ser Met Gly
     50                  55                  60

Gly Gly Tyr Gly Ser Gly Leu Gly Gly Gly Leu Gly Gly Gly Met Gly
 65                  70                  75                  80

Phe Arg Cys Gly Leu Pro Ile Thr Ala Val Thr Val Asn Gln Asn Leu
                 85                  90                  95
```

```
Leu Ala Pro Leu Asn Leu Glu Ile Asp Pro Thr Ile Gln Ala Val Arg
            100                 105                 110

Thr Ser Glu Lys Glu Gln Ile Lys Thr Phe Asn Asn Arg Phe Ala Phe
        115                 120                 125

Leu Ile Asp Lys Val Arg Phe Leu Glu Gln Gln Asn Lys Met Leu Glu
    130                 135                 140

Thr Lys Trp Ser Leu Leu Gln Glu Gln Thr Thr Thr Arg Ser Asn Ile
145                 150                 155                 160

Asp Ala Met Phe Glu Ala Tyr Ile Ser Asn Leu Arg Arg Gln Leu Asp
                165                 170                 175

Gly Leu Gly Asn Glu Lys Met Lys Leu Glu Gly Glu Leu Lys Asn Met
            180                 185                 190

Gln Gly Leu Val Glu Asp Phe Lys Asn Lys Tyr Glu Asp Glu Ile Asn
        195                 200                 205

Lys Arg Ala Ser Val Glu Asn Glu Phe Val Leu Leu Lys Lys Asp Val
    210                 215                 220

Asp Ala Ala Tyr Met Asn Lys Val Glu Leu Glu Ala Lys Val Asp Ala
225                 230                 235                 240

Leu Gln Asp Glu Ile Asn Phe Leu Arg Ala Val Tyr Glu Ala Glu Leu
                245                 250                 255

Arg Glu Leu Gln Ser Gln Ile Lys Asp Thr Ser Val Val Val Glu Met
            260                 265                 270

Asp Asn Ser Arg Asn Leu Asp Met Asp Ser Ile Val Ala Glu Val Arg
        275                 280                 285

Ala Gln Tyr Glu Asp Ile Ala Asn Arg Ser Arg Ala Glu Ala Glu Ser
    290                 295                 300

Trp Tyr Lys Gln Lys Phe Glu Glu Met Gln Ser Thr Ala Gly Gln Tyr
305                 310                 315                 320

Gly Asp Asp Leu Arg Ser Thr Lys Ala Glu Ile Ala Glu Leu Asn Arg
                325                 330                 335

Met Ile Ala Arg Leu Gln Asn Glu Ile Asp Ala Val Lys Ala Gln Arg
            340                 345                 350

Ala Asn Leu Glu Ala Gln Ile Ala Glu Ala Glu Glu Arg Gly Glu Leu
        355                 360                 365

Ala Val Lys Asp Ala Lys Leu Arg Ile Arg Glu Leu Glu Glu Ala Leu
    370                 375                 380

Gln Arg Ala Lys Gln Asp Met Ala Arg Gln Val Arg Glu Tyr Gln Glu
385                 390                 395                 400

Leu Met Asn Val Lys Leu Ala Leu Asp Ile Glu Ile Ala Thr Tyr Arg
                405                 410                 415

Lys Leu Leu Glu Gly Glu Glu Ser Arg Leu Ser Ser Gly Gly Ala Gln
            420                 425                 430

Ala Thr Ile His Val Gln Gln Thr Ser Gly Gly Val Ser Ser Gly Tyr
        435                 440                 445

Gly Gly Ser Gly Ser Gly Phe Gly Tyr Ser Ser Gly Phe Ser Ser Gly
    450                 455                 460

Gly Ser Gly Tyr Gly Ser Gly Ser Gly Phe Gly Ser Gly Ser Gly Tyr
465                 470                 475                 480

Gly Gly Gly Ser Ile Ser Lys Thr Ser Val Thr Thr Val Ser Ser Lys
                485                 490                 495

Arg Tyr
```

<210> SEQ ID NO 3

```
<211> LENGTH: 1589
<212> TYPE: DNA
<213> ORGANISM: Danio rerio
<220> FEATURE:
<221> NAME/KEY: CDS
<222> LOCATION: (86)..(1231)
<220> FEATURE:
<221> NAME/KEY: primer bind
<222> LOCATION: (6)..(26)
<223> OTHER INFORMATION: MCK2
<220> FEATURE:
<221> NAME/KEY: primer bind
<222> LOCATION: (20)..(38)
<223> OTHER INFORMATION: MCK1
<220> FEATURE:
<221> NAME/KEY: polyA signal
<222> LOCATION: (1534)..(1539)

<400> SEQUENCE: 3

cctatttcgg cttggtgaac aggatctgat cccaaggact gttaccactt ttgttgtctt      60

ttgtgcagtg ttagaaaccg caatc atg cct ttc gga aac acc cac aac aac       112
                            Met Pro Phe Gly Asn Thr His Asn Asn
                            1               5

ttc aag ctg aac tac tca gtt gat gag gag tat cca gac ctt agc aag       160
Phe Lys Leu Asn Tyr Ser Val Asp Glu Glu Tyr Pro Asp Leu Ser Lys
10                  15                  20                  25

cac aac aac cac atg gcc aag gtg ctg act aag gaa atg tat ggc aag       208
His Asn Asn His Met Ala Lys Val Leu Thr Lys Glu Met Tyr Gly Lys
                30                  35                  40

ctt agg gac aag cag acc cca cct gga ttc act gtg gat gat gtc atc       256
Leu Arg Asp Lys Gln Thr Pro Pro Gly Phe Thr Val Asp Asp Val Ile
            45                  50                  55

cag act ggt gtt gac aat cca ggc cac ccc ttc atc atg acc gtc ggc       304
Gln Thr Gly Val Asp Asn Pro Gly His Pro Phe Ile Met Thr Val Gly
        60                  65                  70

tgt gtt gct ggt gat gag gag tcc tac gat gtt ttc aag gac ctg ttc       352
Cys Val Ala Gly Asp Glu Glu Ser Tyr Asp Val Phe Lys Asp Leu Phe
    75                  80                  85

gac ccc gtc att tcc gac cgt cac ggt gga tac aag gca act gac aag       400
Asp Pro Val Ile Ser Asp Arg His Gly Gly Tyr Lys Ala Thr Asp Lys
90                  95                  100                 105

cac aag acc gac ctc aac ttt gag aac ctg aag ggt ggt gat gac ctg       448
His Lys Thr Asp Leu Asn Phe Glu Asn Leu Lys Gly Gly Asp Asp Leu
                110                 115                 120

gac ccc aac tac ttc ctg agc agc cgt gtg cgt acc gga cgc agc atc       496
Asp Pro Asn Tyr Phe Leu Ser Ser Arg Val Arg Thr Gly Arg Ser Ile
            125                 130                 135

aag gga tac ccc ctg ccc ccc cac aac agc cgt gga gag cgc aga gct       544
Lys Gly Tyr Pro Leu Pro Pro His Asn Ser Arg Gly Glu Arg Arg Ala
        140                 145                 150

gtg gag aag ctg tct gtt gaa gct ctg agt agc ttg gat gga gag ttc       592
Val Glu Lys Leu Ser Val Glu Ala Leu Ser Ser Leu Asp Gly Glu Phe
    155                 160                 165

aag ggc aag tac tac ccc ctg aag tcc atg act gat gac gag cag gag       640
Lys Gly Lys Tyr Tyr Pro Leu Lys Ser Met Thr Asp Asp Glu Gln Glu
170                 175                 180                 185

cag ctg atc gct gac cac ttc ctc ttt gac aaa ccc gtc tcc ccc ctg       688
Gln Leu Ile Ala Asp His Phe Leu Phe Asp Lys Pro Val Ser Pro Leu
                190                 195                 200

ctg ctg gct gct ggt atg gcc cgt gac tgg ccc gat gcc aga ggc att       736
Leu Leu Ala Ala Gly Met Ala Arg Asp Trp Pro Asp Ala Arg Gly Ile
            205                 210                 215

tgg cac aat gag aac aaa gcc ttc ctg gtc tgg gtg aaa cag gag gat       784
```

```
Trp His Asn Glu Asn Lys Ala Phe Leu Val Trp Val Lys Gln Glu Asp
        220                 225                 230

cac ctg cgt gtc att tcc atg cag aag ggt ggc aac atg aag gaa gtg      832
His Leu Arg Val Ile Ser Met Gln Lys Gly Gly Asn Met Lys Glu Val
    235                 240                 245

ttc aag cgc ttc tgc gtt ggt ctt cag agg att gag gaa att ttc aag      880
Phe Lys Arg Phe Cys Val Gly Leu Gln Arg Ile Glu Glu Ile Phe Lys
250                 255                 260                 265

aag cac aac cat ggg ttc atg tgg aac gag cat ctt ggt ttc gtc ctg      928
Lys His Asn His Gly Phe Met Trp Asn Glu His Leu Gly Phe Val Leu
                270                 275                 280

acc tgc ccc tcc aac ctg ggc aca ggc ctg cgc ggt gga gtc cac gtc      976
Thr Cys Pro Ser Asn Leu Gly Thr Gly Leu Arg Gly Gly Val His Val
            285                 290                 295

aag ctg ccc aag ctc agc aca cat gcc aag ttt gag gag atc ctg acc     1024
Lys Leu Pro Lys Leu Ser Thr His Ala Lys Phe Glu Glu Ile Leu Thr
        300                 305                 310

aga ctg cgc ctg cag aag cgt ggc aca ggg ggt gtg gac acc gct tcc     1072
Arg Leu Arg Leu Gln Lys Arg Gly Thr Gly Gly Val Asp Thr Ala Ser
    315                 320                 325

gtt ggt gga gtg ttt gac att tcc aac gct gac cgt atc ggc tct tca     1120
Val Gly Gly Val Phe Asp Ile Ser Asn Ala Asp Arg Ile Gly Ser Ser
330                 335                 340                 345

gag gtt gag cag gtg cag tgt gtg gtt gat ggt gtc aag ctg atg gtg     1168
Glu Val Glu Gln Val Gln Cys Val Val Asp Gly Val Lys Leu Met Val
                350                 355                 360

gag atg gag aag aag ctg gga gaa ggc cag tcc atc gac agc atg atc     1216
Glu Met Glu Lys Lys Leu Gly Glu Gly Gln Ser Ile Asp Ser Met Ile
            365                 370                 375

cct gcc cag aag taa agcgggaggc ccttccattt ttttcttcgt ctttgtctgt     1271
Pro Ala Gln Lys
        380

tttttacag tccaacagca acgsagagga aaactgctgc tcaaaaagac agtctcacct    1331

ttgcacctgt cttctttcct ttttttccct tcttctctaa tttccatgtc atttcgccat   1391

ctttttttcc actttgtttc ctattaagtc ggtaacatct tgggatcaga tacccggsgc   1451

aggagtgagt gcttgttgct gaggcttcac ctcaatttca gccttggttg taaaaagtga   1511

atcaatcaaa gttgtatttc aaaataaaaa tccccaataa aaaaaaaaaa aaaaaaaaaa   1571

aaaaaaaaaa aaaaaaaa                                                 1589


<210> SEQ ID NO 4
<211> LENGTH: 381
<212> TYPE: PRT
<213> ORGANISM: Danio rerio

<400> SEQUENCE: 4

Met Pro Phe Gly Asn Thr His Asn Asn Phe Lys Leu Asn Tyr Ser Val
  1               5                  10                  15

Asp Glu Glu Tyr Pro Asp Leu Ser Lys His Asn Asn His Met Ala Lys
             20                  25                  30

Val Leu Thr Lys Glu Met Tyr Gly Lys Leu Arg Asp Lys Gln Thr Pro
         35                  40                  45

Pro Gly Phe Thr Val Asp Asp Val Ile Gln Thr Gly Val Asp Asn Pro
     50                  55                  60

Gly His Pro Phe Ile Met Thr Val Gly Cys Val Ala Gly Asp Glu Glu
 65                  70                  75                  80

Ser Tyr Asp Val Phe Lys Asp Leu Phe Asp Pro Val Ile Ser Asp Arg
```

```
                85                  90                  95

His Gly Gly Tyr Lys Ala Thr Asp Lys His Lys Thr Asp Leu Asn Phe
            100                 105                 110

Glu Asn Leu Lys Gly Gly Asp Asp Leu Asp Pro Asn Tyr Phe Leu Ser
        115                 120                 125

Ser Arg Val Arg Thr Gly Arg Ser Ile Lys Gly Tyr Pro Leu Pro Pro
    130                 135                 140

His Asn Ser Arg Gly Glu Arg Arg Ala Val Glu Lys Leu Ser Val Glu
145                 150                 155                 160

Ala Leu Ser Ser Leu Asp Gly Glu Phe Lys Gly Lys Tyr Tyr Pro Leu
                165                 170                 175

Lys Ser Met Thr Asp Asp Glu Gln Glu Gln Leu Ile Ala Asp His Phe
            180                 185                 190

Leu Phe Asp Lys Pro Val Ser Pro Leu Leu Leu Ala Ala Gly Met Ala
        195                 200                 205

Arg Asp Trp Pro Asp Ala Arg Gly Ile Trp His Asn Glu Asn Lys Ala
    210                 215                 220

Phe Leu Val Trp Val Lys Gln Glu Asp His Leu Arg Val Ile Ser Met
225                 230                 235                 240

Gln Lys Gly Gly Asn Met Lys Glu Val Phe Lys Arg Phe Cys Val Gly
                245                 250                 255

Leu Gln Arg Ile Glu Glu Ile Phe Lys Lys His Asn His Gly Phe Met
            260                 265                 270

Trp Asn Glu His Leu Gly Phe Val Leu Thr Cys Pro Ser Asn Leu Gly
        275                 280                 285

Thr Gly Leu Arg Gly Gly Val His Val Lys Leu Pro Lys Leu Ser Thr
    290                 295                 300

His Ala Lys Phe Glu Glu Ile Leu Thr Arg Leu Arg Leu Gln Lys Arg
305                 310                 315                 320

Gly Thr Gly Gly Val Asp Thr Ala Ser Val Gly Gly Val Phe Asp Ile
                325                 330                 335

Ser Asn Ala Asp Arg Ile Gly Ser Ser Glu Val Glu Gln Val Gln Cys
            340                 345                 350

Val Val Asp Gly Val Lys Leu Met Val Glu Met Glu Lys Lys Leu Gly
        355                 360                 365

Glu Gly Gln Ser Ile Asp Ser Met Ile Pro Ala Gln Lys
    370                 375                 380


<210> SEQ ID NO 5
<211> LENGTH: 1104
<212> TYPE: DNA
<213> ORGANISM: Danio rerio
<220> FEATURE:
<221> NAME/KEY: CDS
<222> LOCATION: (75)..(1034)
<220> FEATURE:
<221> NAME/KEY: primer bind
<222> LOCATION: (45)..(64)
<223> OTHER INFORMATION: ARP2
<220> FEATURE:
<221> NAME/KEY: primer bind
<222> LOCATION: (87)..(112)
<223> OTHER INFORMATION: ARK
<220> FEATURE:
<221> NAME/KEY: polyA signal
<222> LOCATION: (1069)..(1074)

<400> SEQUENCE: 5

cgcgtcccta ccgtgagatt ttacaacctt gtctttaaac cggctgttca ccgatccttg     60
```

-continued

```
gaagcactgc aaag atg ccc agg gaa gac agg gcc acg tgg aag tcc aac      110
                Met Pro Arg Glu Asp Arg Ala Thr Trp Lys Ser Asn
                 1               5                  10

tat ttt ctg aaa atc atc caa ctg ctg gat gac ttc ccc aag tgt ttc      158
Tyr Phe Leu Lys Ile Ile Gln Leu Leu Asp Asp Phe Pro Lys Cys Phe
        15                  20                  25

atc gtg ggc gca gac aat gtc ggc tcc aag cag atg cag acc atc cgt      206
Ile Val Gly Ala Asp Asn Val Gly Ser Lys Gln Met Gln Thr Ile Arg
    30                  35                  40

ctg tcc ctg cgg ggc aag gcc gtc gtg ctc atg ggg aaa aac acc atg      254
Leu Ser Leu Arg Gly Lys Ala Val Val Leu Met Gly Lys Asn Thr Met
 45                  50                  55                  60

atg agg aag gcc att cgt ggc cac ctg gaa aac aac cca gct ctg gag      302
Met Arg Lys Ala Ile Arg Gly His Leu Glu Asn Asn Pro Ala Leu Glu
                65                  70                  75

agg ctg ctt ccc cac atc cgc ggg aac gtg ggc ttc gtc ttc acc aag      350
Arg Leu Leu Pro His Ile Arg Gly Asn Val Gly Phe Val Phe Thr Lys
            80                  85                  90

gag gat ctg act gag gtc cga gac ctg ctg ctg gca aac aaa gtg ccc      398
Glu Asp Leu Thr Glu Val Arg Asp Leu Leu Leu Ala Asn Lys Val Pro
        95                 100                 105

gct gct gcc cgt gct ggt gcc atc gcc ccc tgt gag gtg act gtg ccg      446
Ala Ala Ala Arg Ala Gly Ala Ile Ala Pro Cys Glu Val Thr Val Pro
    110                 115                 120

gcc cag aac acc ggg ctc ggt cct gag aag acc tct ttc ttc cag gct      494
Ala Gln Asn Thr Gly Leu Gly Pro Glu Lys Thr Ser Phe Phe Gln Ala
125                 130                 135                 140

ttg gga atc acc acc aag atc tcc aga gga acc att gaa atc ttg agt      542
Leu Gly Ile Thr Thr Lys Ile Ser Arg Gly Thr Ile Glu Ile Leu Ser
                145                 150                 155

gac gtt cag ctt atc aaa cct gga gac aag gtg ggc gcc agc gag gcc      590
Asp Val Gln Leu Ile Lys Pro Gly Asp Lys Val Gly Ala Ser Glu Ala
            160                 165                 170

acg ctg ctg aac atg ctg aac atg ctg aac atc tcg ccc ttc tcc tac      638
Thr Leu Leu Asn Met Leu Asn Met Leu Asn Ile Ser Pro Phe Ser Tyr
        175                 180                 185

ggg ctg atc atc cag cag gtg tat gat aac ggc agt gtc tac agc ccc      686
Gly Leu Ile Ile Gln Gln Val Tyr Asp Asn Gly Ser Val Tyr Ser Pro
    190                 195                 200

gag gtg ctg gac atc act gag gac gcc ctg cac aag agg ttc ctg aag      734
Glu Val Leu Asp Ile Thr Glu Asp Ala Leu His Lys Arg Phe Leu Lys
205                 210                 215                 220

ggt gtg agg aac atc gcc agt gtg tgt ctg cag atc ggc tac cca act      782
Gly Val Arg Asn Ile Ala Ser Val Cys Leu Gln Ile Gly Tyr Pro Thr
                225                 230                 235

ctt gct tcc atc cct cac act atc atc aat gga tac aag agg gtc ctg      830
Leu Ala Ser Ile Pro His Thr Ile Ile Asn Gly Tyr Lys Arg Val Leu
            240                 245                 250

gct gtc act gtc gaa aca gac tac aca ttc ccc ttg gct gag aag gtg      878
Ala Val Thr Val Glu Thr Asp Tyr Thr Phe Pro Leu Ala Glu Lys Val
        255                 260                 265

aag gcc tac ctg gct gat ccc acc gct ttc gct gtt gca gcc cct gtt      926
Lys Ala Tyr Leu Ala Asp Pro Thr Ala Phe Ala Val Ala Ala Pro Val
    270                 275                 280

gcg gca gct aca gag cag aaa tcc gct gct cct gcg gct aaa gag gag      974
Ala Ala Ala Thr Glu Gln Lys Ser Ala Ala Pro Ala Ala Lys Glu Glu
285                 290                 295                 300

gca ccc aag gag gat tct gag gag tct gat gaa gac atg ggc ttc ggc     1022
Ala Pro Lys Glu Asp Ser Glu Glu Ser Asp Glu Asp Met Gly Phe Gly
```

```
                305                 310                 315

ctg ttt gat taa accagacacc gaatatccat gtctgtttaa catcaataaa         1074
Leu Phe Asp

acatctggaa aaaaaaaaaa aaaaaaaaaa                                    1104


<210> SEQ ID NO 6
<211> LENGTH: 319
<212> TYPE: PRT
<213> ORGANISM: Danio rerio

<400> SEQUENCE: 6

Met Pro Arg Glu Asp Arg Ala Thr Trp Lys Ser Asn Tyr Phe Leu Lys
  1               5                  10                  15

Ile Ile Gln Leu Leu Asp Asp Phe Pro Lys Cys Phe Ile Val Gly Ala
             20                  25                  30

Asp Asn Val Gly Ser Lys Gln Met Gln Thr Ile Arg Leu Ser Leu Arg
         35                  40                  45

Gly Lys Ala Val Val Leu Met Gly Lys Asn Thr Met Met Arg Lys Ala
     50                  55                  60

Ile Arg Gly His Leu Glu Asn Asn Pro Ala Leu Glu Arg Leu Leu Pro
 65                  70                  75                  80

His Ile Arg Gly Asn Val Gly Phe Val Phe Thr Lys Glu Asp Leu Thr
                 85                  90                  95

Glu Val Arg Asp Leu Leu Leu Ala Asn Lys Val Pro Ala Ala Ala Arg
            100                 105                 110

Ala Gly Ala Ile Ala Pro Cys Glu Val Thr Val Pro Ala Gln Asn Thr
        115                 120                 125

Gly Leu Gly Pro Glu Lys Thr Ser Phe Phe Gln Ala Leu Gly Ile Thr
    130                 135                 140

Thr Lys Ile Ser Arg Gly Thr Ile Glu Ile Leu Ser Asp Val Gln Leu
145                 150                 155                 160

Ile Lys Pro Gly Asp Lys Val Gly Ala Ser Glu Ala Thr Leu Leu Asn
                165                 170                 175

Met Leu Asn Met Leu Asn Ile Ser Pro Phe Ser Tyr Gly Leu Ile Ile
            180                 185                 190

Gln Gln Val Tyr Asp Asn Gly Ser Val Tyr Ser Pro Glu Val Leu Asp
        195                 200                 205

Ile Thr Glu Asp Ala Leu His Lys Arg Phe Leu Lys Gly Val Arg Asn
    210                 215                 220

Ile Ala Ser Val Cys Leu Gln Ile Gly Tyr Pro Thr Leu Ala Ser Ile
225                 230                 235                 240

Pro His Thr Ile Ile Asn Gly Tyr Lys Arg Val Leu Ala Val Thr Val
                245                 250                 255

Glu Thr Asp Tyr Thr Phe Pro Leu Ala Glu Lys Val Lys Ala Tyr Leu
            260                 265                 270

Ala Asp Pro Thr Ala Phe Ala Val Ala Ala Pro Val Ala Ala Ala Thr
        275                 280                 285

Glu Gln Lys Ser Ala Ala Pro Ala Ala Lys Glu Glu Ala Pro Lys Glu
    290                 295                 300

Asp Ser Glu Glu Ser Asp Glu Asp Met Gly Phe Gly Leu Phe Asp
305                 310                 315


<210> SEQ ID NO 7
<211> LENGTH: 2241
<212> TYPE: DNA
```

<213> ORGANISM: Danio rerio
<220> FEATURE:
<221> NAME/KEY: TATA signal
<222> LOCATION: (2103)..(2108)
<220> FEATURE:
<221> NAME/KEY: primer bind
<222> LOCATION: (2221)..(2241)
<223> OTHER INFORMATION: CK2
<220> FEATURE:
<221> NAME/KEY: misc feature
<222> LOCATION: (2142)..(2235)
<223> OTHER INFORMATION: Identical to the 5' CK cDNA

<400> SEQUENCE: 7

```
ccttcccttc tacttttgac gtccttttaa gattactcat ctcaaacacc catacaaagg     60
tcacacctgg tttatactat gatagttgta cagtgctggc tgtgacaccc aactgctgcc    120
aattgtctga ctatgcaggg tgtctatgcg tatagtttac agttagacca aagtgtgctg    180
gtgtgtgaag taacaaatga caaatactca aattgtaatt tactaagtag tttaaaaatg    240
tagtgcagtg ttggtacttt tatttcactt ttattcttgt ctatgtggat tagacaaatc    300
acatagaagg taaatcacat cataatgaac agcaaactgt ttgccagcat taaaagaaga    360
agactgctta gatgcatgtc actgatgaga aaataacttt aaacgcacac aagacggcac    420
gtaccccaac gcagtgggga cgttgcattt gaactcaacg tcaggtcgat gtcaatgttc    480
ctaatgatgt tacagcttga tgttatgcgg ggattatggt tgccatacct gatgaataaa    540
ggttcgacat tggattttgg tcgctttcca cctatgacat cgttattgga cgtcaaaata    600
aatttaggtc accacaacct atatttaacc tgctgggcaa taactaaatg cactacagaa    660
taaatgcatc agcttttcac agcataatac aaaagctact tttcactcat actttgagta    720
acatttttag gcatgtattg atatttttac cagccctccc catacataat cgtatgttta    780
acattagctt tgttagccgc tagcattact gagcttgtgc atgaaagcag atttggagct    840
gatgattgcc gtaccatgat ctcacacctt gacgattgcg taatgctatt aaatgcccat    900
atttcgtgtt gacttgcacg agaaatgaga tgggaacatt tatcagtggt cattaaatac    960
tatttttgtg ttagcttagc tgcagttttt aactattgta attaagtagt ttttctcaga   1020
tgtactttta ctttcccttg agtacatttt ccttccttca acctgcagtc actactttat   1080
agtcctgtga ttcctgtcca atcaaattgc taccttaaga catgggccat ttataattgc   1140
tgtcaaaaat atttacacgc attaacccag agatgatgga tgtttactgt atgatgaccg   1200
aagacgtcaa catggcgtta ggttgacgtt tgtttagaaa tgaaaattag gttgacgtca   1260
aacatccaat ctaaaatcat atatcaatgt atgttacccc tatgacgtct atcagacgtt   1320
tgtcattatt tgacgttggt ttaagatgtt acacaaccta aatccaccaa atattaactt   1380
acaatatcct tagatgctgg ctagactttg taatattaac atcttatgat gttgtgtgcc   1440
tgttacgttt acacacatgt aaattacatg tcactactta ctactcttga gtacttttaa   1500
atatttacaa ctgatacttt tactcgcact tatgattttt cagtactctt tccactactg   1560
cacatatggt ggagtttaga gccataatct gtgcagaatt gtgtgtgtgc acattttcca   1620
atatcaatac agaaggaaac tgtgttccct gttcccttgt aaatctcaac aatgcaactg   1680
ttcagctcag ggggaaaaat gccctgccag atccaaacgg ctggcaaaag tgaatggaaa   1740
aaagcctttc attaatgtga aagttgctgc gcgccccacc cagataaaaa gagcagaggt   1800
taacatgctc tctacggctg tccagccaac cagatactga ggcagaaaca cacccgctgg   1860
cagatggtga gagctacact gtcttttcca gagtttctac tggaatgcct gtcctcaagt   1920
```

```
ctcaagcctc tccttgcatt ctctcattcc acctggggca aagccccagg ctgggtgtga   1980

caacatttat cttaccactt tctctctgta cctgtctaac aggtagggtg tgtgtgagag   2040

tgcgtatgtg tgcaagtgcg tgtgtgtgtg agagcagtca gctccaccct ctcaagagtg   2100

tgtataaaat tggtcagcca gctgctgaga gacacgcaga gggactttga ctctcctttg   2160

tgagcaacct cctccactca ctcctctctc agagagcact ctcgtacctc cttctcagca   2220

actcaaagac acaggatccg g                                             2241
```

<210> SEQ ID NO 8
<211> LENGTH: 1456
<212> TYPE: DNA
<213> ORGANISM: Danio rerio
<220> FEATURE:
<221> NAME/KEY: TATA signal
<222> LOCATION: (1389)..(1394)
<220> FEATURE:
<221> NAME/KEY: primer bind
<222> LOCATION: (1433)..(1456)
<223> OTHER INFORMATION: MCK2
<220> FEATURE:
<221> NAME/KEY: misc feature
<222> LOCATION: (1428)..(1453)
<223> OTHER INFORMATION: Identical to the 5' MCK cDNA

<400> SEQUENCE: 8

```
gaattgcaaa gtcagagtaa taaaatgaaa ccaaaaaaca tttttaaata tacttgtctc     60

tgtggcttaa tcttggctga tgtgtgtgtg tgtgtgtgtg tacttgacag ctgctagtga    120

gcatgtgcac catgacaggc ctgttattca cacttggtgc catgttggag actgttcggc    180

cagctatagt tttcttcaca gagtcctggg tcacctaatg tcacaaggaa gaaacatgtt    240

acatgttaaa atgtgacatt caaattgtag tgcattactt aacgaaacgc attacacaag    300

ttacagctta aaagattgct agacagaaaa accagggagg ggttttccca taatatccag    360

tgagactcta ggagcgggaa cactaacagg cctccctgag tgagaacatt gcatgtgcgc    420

gtgacagaaa accagagatg gaaatacctt cttttgaatt gcataattgc ttaaaagaag    480

acacaacagg gatagttcac ccaaaaaaca gaccattctt tttttctgtt gaacaaaaat    540

taagatattt tgaagaatgc ttaccgaata acttccatat ttggaaacta attacagtga    600

aagtcaatgg gtcttccagc attttttcaa tataccttac tttgagttca aaagaaaaac    660

acatctcaaa taggtttgag gttgaataaa catttttcat tttggggtgg actatcccta    720

attatttgac acttaagatt tatagtaaat cattttatag actttctccc cttattaaac    780

atggttgaat ttatcttcat gtttatgtct gggttgtgct tttttgaaaa gatttccctg    840

tcaaatgttt ttgtgtatgg ttggcgcaca atagactgaa ctggcctatc acacagactt    900

tcataacaac tccagttgat gccctttcac cctcagtgta taaatatggc gtctgacatg    960

agcagattaa acacgacact gcaacaactt tacctgtaaa aatacaaatt gagtttgcac   1020

ccagaatcat gtggtgaacg aagcctacca agagattttt gaaagccatc ggcctgacac   1080

gcgcacttct gatatctgtg gtatgtttgg caaaagtgct gctcagcctt tttagcatgg   1140

cagatcctcc acatcccatc acccctcctt caacctattc cctcctggaa agctatgtat   1200

ggggcgggaa gtgtaaatgg atatgggaag gaagggggc accacccaca gctgccacct    1260

catctaggat gcctggggcc taaattgaag cctttcttac actaaacagg gcataagaga   1320

ccagcgccag ccaatcataa ttcagtgagc tctaaaatgg gccagccaat ggctgcaggg   1380

gctagaggta tatatatcca aatcaaactc ttcttgcttg ggtgacccct atttcggctt   1440
```

```
ggtgaacagg atccgg                                                    1456


<210> SEQ ID NO 9
<211> LENGTH: 2205
<212> TYPE: DNA
<213> ORGANISM: Danio rerio
<220> FEATURE:
<221> NAME/KEY: primer bind
<222> LOCATION: (2179)..(2205)
<223> OTHER INFORMATION: ARP2
<220> FEATURE:
<221> NAME/KEY: misc feature
<222> LOCATION: (2153)..(2199)
<223> OTHER INFORMATION: Identical to the 5' ARP cDNA
<220> FEATURE:
<221> NAME/KEY: intron
<222> LOCATION: (792)..(2152)
<220> FEATURE:
<221> NAME/KEY: misc feature
<222> LOCATION: (775)..(791)
<223> OTHER INFORMATION: Identical to the 5' ARP cDNA

<400> SEQUENCE: 9

atctgtatta agaaacactt aaaatatata tgcgttacga attaaaaaca aaacacgatc     60

attttaattt gtgttgtata attttacatt ttgtaagtat tatttttata aaaaatatat    120

agaaataata caaatttgtt tacagtattc ttagttattg caataaacga attttatata    180

gaaagagaaa gagttttatt ataagatgtt caatttaaaa aatggcagaa aatagaaaaa    240

tgattgtcaa gatgataaaa gtcagtttag acaaaaaaat aagatgaaaa acatcaaaat    300

agataataaa gtgacttttt tgggcggacc aaatttccct attaatggtc aattcattaa    360

aatacattca ttaaaataaa ggtattgcga tgaatttaga tgcacagtga ttttggttct    420

gtgcagattt ttggctgttg ttagaaggga tacatctgcg gccgaaagtt aacgggaact    480

atttacattc tttgctatta aattatccat tatttgtatt ttattacccc aaccgtaaac    540

tcaaccctca cagtaatgta aaaatattat ttattgtttt atagcgtcac agaatgatgc    600

tatattgacc gcagctgtat cctttctaag tgcgactgta caaatacgca ctgaccgtga    660

cagacacgtg cattgaccaa tcagcgcaca gatacgcatt ttccgcgcga ttctgattgg    720

atgatcgact gatactaata ttgtgccgct tcctttcgcg gcctctttct ttcacgcgtc    780

cctaccgtga ggtaaggctg acgccgctct tgtggcggtt tcttaaaatg tgttaataaa    840

taacatcata agaggtcacg agaaggtcta cgtgtgttta atatcagcgg cggttattat    900

tatgcgttta aagcttgtgt aatgattttt acagtaaaag ttagcactag cctgttagca    960

caggcctcgt gcgccatgtg tgacgcgacg ttttaatagc atcttatttg attttgatga   1020

tccgattctg atattaatca tatttatgcg taaaatgtgt gatgggtctg ctagtggaca   1080

ttacatgcta gtacttgtgc tagtcggtcg atccacattg agatgttgcg ctatttgcca   1140

ttttaaaacc agttactctc attttagtga aatattctta agccactaag ttaaaatttg   1200

tcaatcacat ataattgtgt ttatgtttta tttgagtcat cataccaggt aatagtttta   1260

tttatattag tatgtacaat ttggcataaa ctgccttcgg ttttgattga catctacttt   1320

gtaaaggtaa tcttaaaggg gtaaaggctc acccaaaaga caattcaccg tcaagtgttt   1380

tcaaatctta tgagtttctt aatgaacatg gtatgttttg gagaaaactg gaaaccaact   1440

accataatac aaatacagga aaaatatact atagaagtcg atggttacag gttttctgca   1500

ttcaaaatat ctacacaagt gtttaatgga aggaactcaa gtgatttgaa aagttaaggg   1560

tgcataaatc agttttcatt tgggtgagct gtctctaaac atttgattta gacacctcag   1620
```

-continued

```
gcagtggtca ccaagcttgt tcctgaaggg ccagtgtcct acagatttta gctccaaccc   1680

taattaaaca cacctgaaca agctaatcaa ggtcttacta ggtatgtttg aaacatccag   1740

gcaggtgtgt tgatgcaaga tagagctaaa ccctgcaggg acaatggccc aacaggattg   1800

gtgacccctg cctcaagcca tcacaaatgc attatggtat taagaaatgt gcaggttcag   1860

ttatggacag gctgttgcag tgcttgttcg tcgttcccac tgcacaaatg aacatgattc   1920

cttctatccc tgtctgtctg catctcatga cttgcaggga cgctggtctc agacacgttt   1980

atagcagtaa atcaaataca atagtgctct gattatcttt aaatatttga aagcttataa   2040

taggcaacca aattacctgg aaacagttta caaacagtaa ttcatatttt gtcatttaat   2100

aagatgcaca caaggcaggt gtaaaagtat tgcttgtgtt tgtaatcctc agattttaca   2160

accttgtctt taaaccggct gttcaccgat ccttggaagg gatcc                   2205


<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence:
      Cytokeratin - gene specific primer

<400> SEQUENCE: 10

cgctggagta agagatagac ctgg                                            24


<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence: Cytokeratin
      gene specific primer
<220> FEATURE:
<221> NAME/KEY: misc feature
<222> LOCATION: (1)..(6)
<223> OTHER INFORMATION: Introduced for restriction site
<220> FEATURE:
<221> NAME/KEY: misc feature
<222> LOCATION: (3)..(8)
<223> OTHER INFORMATION: BamHI site

<400> SEQUENCE: 11

ccggatcctg tgtctttgag ttgctg                                          26


<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence:
      Muscle creatine kinase gene specific primer
<220> FEATURE:
<221> NAME/KEY: misc feature
<222> LOCATION: (3)..(8)
<223> OTHER INFORMATION: BamHI site

<400> SEQUENCE: 12

ccggatcctt gggatcagat cctg                                            24


<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence:
      Muscle creatine kinase gene specific primer
```

<220> FEATURE:
<221> NAME/KEY: misc feature
<222> LOCATION: (1)..(3)
<223> OTHER INFORMATION: Introduced for restriction site
<220> FEATURE:
<221> NAME/KEY: misc feature
<222> LOCATION: (3)..(3)
<223> OTHER INFORMATION: BamHI site

<400> SEQUENCE: 13
ccggatcctg ttcaccaagc cgaa 24

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Acidic ribosomal protein PO gene specific primer

<400> SEQUENCE: 14
tagttggact tccacgtgcc ctgtc 25

<210> SEQ ID NO 15
<211> LENGTH: 26
<212> TYPE: DNA
<213> ORGANISM: Artificial Sequence
<220> FEATURE:
<223> OTHER INFORMATION: Description of Artificial Sequence: Acidic ribosomal protein PO gene specific primer
<220> FEATURE:
<221> NAME/KEY: misc feature
<222> LOCATION: (1)..(7)
<223> OTHER INFORMATION: Introduced for restriction site
<220> FEATURE:
<221> NAME/KEY: misc feature
<222> LOCATION: (1)..(6)
<223> OTHER INFORMATION: BamHI site

<400> SEQUENCE: 15
ggatcccttc caaggatcgg tgaaca 26

<210> SEQ ID NO 16
<211> LENGTH: 51
<212> TYPE: DNA
<213> ORGANISM: Artificial Sequence
<220> FEATURE:
<223> OTHER INFORMATION: Description of Artificial Sequence: Oligonucleotide for linker used in linker-mediated PCR

<400> SEQUENCE: 16
gttcatcttt acaagctagc gctgaacaat gctgtggaca agcttgaatt c 51

<210> SEQ ID NO 17
<211> LENGTH: 10
<212> TYPE: DNA
<213> ORGANISM: Artificial Sequence
<220> FEATURE:
<223> OTHER INFORMATION: Description of Artificial Sequence: Oligonucleotide for linker used in linker-mediated PCR
<220> FEATURE:
<221> NAME/KEY: misc feature
<222> LOCATION: (10)..(10)
<223> OTHER INFORMATION: n is a dideoxycytidine

<400> SEQUENCE: 17 gaattcaagn 10

<210> SEQ ID NO 18

```
<211> LENGTH: 21
<212> TYPE: DNA
<213> ORGANISM: Artificial Sequence
<220> FEATURE:
<223> OTHER INFORMATION: Description of Artificial Sequence:
      linker specific primer

<400> SEQUENCE: 18

gttcatcttt acaagctagc g                                              21


<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence:
      linker specific primer

<400> SEQUENCE: 19

tcctgaacaa tgctgtggac                                                20


<210> SEQ ID NO 20
<211> LENGTH: 1392
<212> TYPE: DNA
<213> ORGANISM: Danio rerio
<220> FEATURE:
<221> NAME/KEY: CDS
<222> LOCATION: (42)..(551)
<220> FEATURE:
<221> NAME/KEY: primer bind
<222> LOCATION: (6)..(28)
<223> OTHER INFORMATION: M2
<220> FEATURE:
<221> NAME/KEY: primer bind
<222> LOCATION: (23)..(45)
<223> OTHER INFORMATION: M1
<220> FEATURE:
<221> NAME/KEY: polyA signal
<222> LOCATION: (797)..(802)
<220> FEATURE:
<221> NAME/KEY: polyA signal
<222> LOCATION: (1351)..(1357)

<400> SEQUENCE: 20

ctcttcttga tcttcttaga cttcacacat accgtctcga c atg gca ccc aag aag     56
                                              Met Ala Pro Lys Lys
                                               1               5

gcc aag agg agg gca gca gga gga gag ggt tcc tcc aac gtc ttc tcc      104
Ala Lys Arg Arg Ala Ala Gly Gly Glu Gly Ser Ser Asn Val Phe Ser
                10                  15                  20

atg ttt gag cag agc cag att cag gag tac aaa gag gct ttc aca atc      152
Met Phe Glu Gln Ser Gln Ile Gln Glu Tyr Lys Glu Ala Phe Thr Ile
            25                  30                  35

att gac cag aac aga gac ggt atc atc agc aaa gac gac ctt agg gac      200
Ile Asp Gln Asn Arg Asp Gly Ile Ile Ser Lys Asp Asp Leu Arg Asp
        40                  45                  50

gtg ttg gcc tca atg ggc cag ctg aat gtg aag aat gag gag ctg gag      248
Val Leu Ala Ser Met Gly Gln Leu Asn Val Lys Asn Glu Glu Leu Glu
    55                  60                  65

gcc atg atc aag gaa gcc agc ggc cca atc aac ttc acc gtt ttc ctc      296
Ala Met Ile Lys Glu Ala Ser Gly Pro Ile Asn Phe Thr Val Phe Leu
 70                  75                  80                  85

acc atg ttc gga gag aag ttg aag ggt gct gac ccc gaa gac gtc atc      344
Thr Met Phe Gly Glu Lys Leu Lys Gly Ala Asp Pro Glu Asp Val Ile
                90                  95                 100

gtg tct gcc ttc aag gtg ctg gac cct gag ggc act gga tcc atc aag      392
Val Ser Ala Phe Lys Val Leu Asp Pro Glu Gly Thr Gly Ser Ile Lys
```

```
            105                 110                 115

aag gaa ttc ctt gag gag ctt ttg acc act cag tgc gac agg ttc acc      440
Lys Glu Phe Leu Glu Glu Leu Leu Thr Thr Gln Cys Asp Arg Phe Thr
        120                 125                 130

gca gag gag atg aag aat ctg tgg gcc gcc ttc ccc cca gat gtg gct      488
Ala Glu Glu Met Lys Asn Leu Trp Ala Ala Phe Pro Pro Asp Val Ala
    135                 140                 145

ggc aat gtt gac tac aag aac atc tgc tac gtc atc aca cac gga gag      536
Gly Asn Val Asp Tyr Lys Asn Ile Cys Tyr Val Ile Thr His Gly Glu
150                 155                 160                 165

gag aag gag gag taa acaaccttgg aatagaggaa acgaagagaa gaacatgcat      591
Glu Lys Glu Glu

cctcacagct taatctccag tctgttgtct ggccttctct aacttttgtt tttccttcct    651

ccctttcttg ctttctacca tcgttgttac tccaagcact tacactctcc atcttaccaa    711

agacttgtct cgctgggact gaattgggag ggtggagagg aacacgacca cagtgtctgt    771

cgagtgggga catgggattg ttttcaataa aatgaacatc atttctgtat ctctcacatt    831

ctctctttct ctctgtttct cactcattac ccacaacccc tctctttcat ttcagtcaag    891

cttgcatgta agtcgctgct tcttctgctg cagtcttagg agttgaaacg aaggcatcta    951

tagtttgggg ctgaaacatc tctctagatc aatgtggaag agtgctcact ctgaggggga   1011

aagaagcacg atggagtgat ctcactctat aatagaggaa ccagtcatca ttctcatttc   1071

ctcctctggt ggttgactaa aaagagaaag agaaaatgag ggttttgtgc tgagtgagtt   1131

tagcctccta aaagcgatgc cgagctcatc acagagggag tgagagggac agaccatcct   1191

aggaagagag gagagcaggg actgaaagaa aacataacct cttcactccc cctctcccct   1251

cctcttctct atttctctgt ccatcttttc ttttttcttt tttctttttt gctttctgca   1311

tctgggcctg ctttgctctg ccaaacctct cctgtaacca ataaaaagac acaaactgtg   1371

aataaaaaaa aaaaaaaaaa a                                              1392


<210> SEQ ID NO 21
<211> LENGTH: 169
<212> TYPE: PRT
<213> ORGANISM: Danio rerio

<400> SEQUENCE: 21

Met Ala Pro Lys Lys Ala Lys Arg Arg Ala Ala Gly Gly Glu Gly Ser
  1               5                  10                  15

Ser Asn Val Phe Ser Met Phe Glu Gln Ser Gln Ile Gln Glu Tyr Lys
             20                  25                  30

Glu Ala Phe Thr Ile Ile Asp Gln Asn Arg Asp Gly Ile Ile Ser Lys
         35                  40                  45

Asp Asp Leu Arg Asp Val Leu Ala Ser Met Gly Gln Leu Asn Val Lys
     50                  55                  60

Asn Glu Glu Leu Glu Ala Met Ile Lys Glu Ala Ser Gly Pro Ile Asn
 65                  70                  75                  80

Phe Thr Val Phe Leu Thr Met Phe Gly Glu Lys Leu Lys Gly Ala Asp
                 85                  90                  95

Pro Glu Asp Val Ile Val Ser Ala Phe Lys Val Leu Asp Pro Glu Gly
            100                 105                 110

Thr Gly Ser Ile Lys Lys Glu Phe Leu Glu Glu Leu Leu Thr Thr Gln
        115                 120                 125

Cys Asp Arg Phe Thr Ala Glu Glu Met Lys Asn Leu Trp Ala Ala Phe
    130                 135                 140
```

```
Pro Pro Asp Val Ala Gly Asn Val Asp Tyr Lys Asn Ile Cys Tyr Val
145                 150                 155                 160

Ile Thr His Gly Glu Glu Lys Glu Glu
                165


<210> SEQ ID NO 22
<211> LENGTH: 2054
<212> TYPE: DNA
<213> ORGANISM: Danio rerio
<220> FEATURE:
<221> NAME/KEY: TATA signal
<222> LOCATION: (1983)..(1989)
<220> FEATURE:
<221> NAME/KEY: enhancer
<222> LOCATION: (142)..(148)
<223> OTHER INFORMATION: E-box, canntg
<220> FEATURE:
<221> NAME/KEY: enhancer
<222> LOCATION: (452)..(457)
<223> OTHER INFORMATION: E-box, canntg
<220> FEATURE:
<221> NAME/KEY: enhancer
<222> LOCATION: (1095)..(1100)
<223> OTHER INFORMATION: E-box, canntg
<220> FEATURE:
<221> NAME/KEY: enhancer
<222> LOCATION: (1278)..(1283)
<223> OTHER INFORMATION: E-box, canntg
<220> FEATURE:
<221> NAME/KEY: enhancer
<222> LOCATION: (1362)..(1367)
<223> OTHER INFORMATION: E-box, canntg
<220> FEATURE:
<221> NAME/KEY: enhancer
<222> LOCATION: (1385)..(1390)
<223> OTHER INFORMATION: E-box, canntg
<220> FEATURE:
<221> NAME/KEY: enhancer
<222> LOCATION: (523)..(532)
<223> OTHER INFORMATION: Potential MEF2 binding site, yta(w)4tar
<220> FEATURE:
<221> NAME/KEY: enhancer
<222> LOCATION: (606)..(615)
<223> OTHER INFORMATION: Potential MEF2 binding site, yta(w)4tar
<220> FEATURE:
<221> NAME/KEY: enhancer
<222> LOCATION: (697)..(706)
<223> OTHER INFORMATION: Potential MEF2 binding site, yta(w)4tar
<220> FEATURE:
<221> NAME/KEY: enhancer
<222> LOCATION: (1490)..(1499)
<223> OTHER INFORMATION: Potential MEF2 binding site, yta(w)4tar
<220> FEATURE:
<221> NAME/KEY: enhancer
<222> LOCATION: (1640)..(1649)
<223> OTHER INFORMATION: Potential MEF2 binding site, yta(w)4tar
<220> FEATURE:
<221> NAME/KEY: enhancer
<222> LOCATION: (1956)..(1965)
<223> OTHER INFORMATION: Potential MEF2 binding site, yta(w)4tar
<220> FEATURE:
<223> OTHER INFORMATION: Transcription start site at residue 2012
<220> FEATURE:
<221> NAME/KEY: primer bind
<222> LOCATION: (2032)..(2054)
<223> OTHER INFORMATION: M2
<220> FEATURE:
<221> NAME/KEY: misc feature
<222> LOCATION: (2027)..(2054)
<223> OTHER INFORMATION: Identical to the 5' MLC2f cDNA

<400> SEQUENCE: 22

tgcatgcctg gcaggtccac tctagaggac tactagtcat atgcgattct gaacaatgct     60

ggaatgagcc accaactcat ccagtgtatt accctacact gggaaacacc caaatctgtc    120
```

```
tgttatattt gtgcatatac attagattag aagctgtcac tgcggtggta ccttttcaaa    180

ttgatacctc aaaagtatat attagtgcct tttaggtact aatatatacc cttgaggttt    240

tcatttggaa aggtaccacc ccagtgacag aaatctggag cttatttaac aaaataactt    300

tatttatatg ttattgaaaa atattaaata agcaaaacaa tggaaaaaaa ttagttcaaa    360

atttagcttt atttaaattg ttttatcttt aatatagctg tttaataaat ctgttttgtt    420

actgagagat ggagaaaaat attcattttc ctgtaattat ctgtttttct aggtactgta    480

caagcaggag caaaacaagc cgacagactc gggaatgcac aacaaactca agggggcaa    540

gagagcaagg agcgctcaag attgtttagc ctgccttccc aaaaaaaaac tgtcttaagc    600

caaccactca gagggctgta gtgtgctgac cgtgcttgtc cacagggcag cttcccacaa    660

gtgaggtcat aggtcgatcg gcagagagag atgggcatgg ccatgtggac gggtgtggtg    720

actatactag gaaaagcatt aaaacctatt aagacaccag aacgtcctct tatatatcag    780

tcattggctc aaaaatctct ggattgaaat atccaacaag taatcctgca agataagcca    840

ggagggagtt gcgtcccctt tagactcagt atgtgattgt atgaagctca aacagtccct    900

gtggacagct tgaattcaat tcgccacaga ttttatgcag cggatgccca tccagttgca    960

ttttaaatta atatttttaa taggaagcta tcagtacact ctcagaaata aatggtccgc   1020

aggtacatat ttgtacttaa agggtccata aaaaatttta agagaaacac ttttgtactt   1080

tattatggac ctttaaggta caaattttta ctcacgccct ttatttctga gagtgaagct   1140

atgataacgg tccaaaaact actacaccca caaatttata aacaggggaa aatcaagaga   1200

atttgtaggt tgtaattttt ttgttgcaat caattttgtg actaaaatat tattttaata   1260

taaatgcacc aaaatacatt gcctatattc aaaatgggct gtactcaatt actctaagca   1320

aaataatgct aatcttaaac aattttggaa acaggatatc aaattagtct aaagaaagaa   1380

aacagtgact gatgaattag acaagaaaaa tattttggtc accacagctg ttccttatgc   1440

ctcaaatttc tcttcatgag ggtccaacat catctaaaaa ctgggaaaaa ggggtaatta   1500

atggcacctc acagtcactg aagtgaccgg agagagagag agagagagag agtgctgaat   1560

ggggcacttg aaccgaaatc ttacagcatc ttcgattagg gctgatttga aataagggtt   1620

ccagggcgtg aacaaatatg aacaacataa ccatcaggat ctatcactgc aaccctcccc   1680

gtattgatct gctgctaatc taactttagg ggctacagct cattcatttc aaattgagtt   1740

tacgtcccca tgtccttatt agacaacgcg agacatgcag gccgctgcca tcagtatcag   1800

attcatccca ttccaagact ccaatagcta tttctgagca ctgtaagatg atagtacatc   1860

ccagccggtg tccctccatc actttccccc tacctcatag tttttcctct ttctctctcg   1920

gtctgctatt tcccaaacct cacttaaggt tgggtctata attagcaagg ggccttcgtc   1980

agtatataag cccctcaagt acaggacact acgcggcttc agacttctct tcttgatctt   2040

cttagacttc acac                                                     2054
```

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: MLC2F gene specific primer M1

<400> SEQUENCE: 23

```
ccatgtcgag acggtatgtg tga                                             23
```

-continued

```
<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence:
      MLC2F gene specific primer M2

<400> SEQUENCE: 24

gtgtgaagtc taagaagatc aag                                         23
```

CHIMERIC GENE CONSTRUCTS FOR GENERATION OF FLUORESCENT TRANSGENIC ORNAMENTAL FISH

CROSS REFERENCE TO RELATED APPLICATIONS

The present application is a continuation of U.S. patent application Ser. No. 13/334,444, filed on Dec. 22, 2011, now U.S. Pat. No. 8,378,169, which is a continuation of U.S. patent application Ser. No. 11/749,032, filed on May 15, 2007, now U.S. Pat. No. 8,153,858, which is a continuation of U.S. patent application Ser. No. 10/605,708, filed on Oct. 21, 2003, now U.S. Pat. No. 7,834,239, which is a division of U.S. patent application Ser. No. 09/913,898, filed Oct. 3, 2001, now U.S. Pat. No. 7,135,613 which is a nationalization of International Application No. PCT/SG1999/000079, filed Jul. 16, 1999, claiming priority over a Singapore application, Ser. No. 9903367-2, filed Jul. 14, 1999, and an earlier Singapore application, Serial No. 9900811-2, filed Feb. 18, 1999, all of which are incorporated herein by reference in their entirety.

BACKGROUND OF INVENTION

This invention relates to fish gene promoters and chimeric gene constructs with these promoters for generation of transgenic fish, particularly fluorescent transgenic ornamental fish.

Transgenic technology involves the transfer of a foreign gene into a host organism enabling the host to acquire a new and inheritable trait. The technique was first developed in mice by Gordon et al. (1980). They injected foreign DNA into fertilized eggs and found that some of the mice developed from the injected eggs retained the foreign DNA. Applying the same technique, Palmiter et al. (1982) have introduced a chimeric gene containing a rat growth hormone gene under a mouse heavy metal-inducible gene promoter and generated the first batch of genetically engineered supermice, which are almost twice as large as non-transgenic siblings. This work has opened a promising avenue in using the transgenic approach to provide to animals new and beneficial traits for livestock husbandry and aquaculture.

In addition to the stimulation of somatic growth for increasing the gross production of animal husbandry and aquaculture, transgenic technology also has many other potential applications. First of all, transgenic animals can be used as bioreactors to produce commercially useful compounds by expression of a useful foreign gene in milk or in blood. Many pharmaceutically useful protein factors have been expressed in this way. For example, human αl-antitrypsin, which is commonly used to treat emphysema, has been expressed at a concentration as high as 35 mg/ml (10% of milk proteins) in the milk of transgenic sheep (Wright et al., 1991). Similarly, the transgenic technique can also be used to improve the nutritional value of milk by selectively increasing the levels of certain valuable proteins such as caseins and by supplementing certain new and useful proteins such as lysozyme for antimicrobial activity (Maga and Murray, 1995). Second, transgenic mice have been widely used in medical research, particularly in the generation of transgenic animal models for human disease studies (Lathe and Mullins, 1993). More recently, it has been proposed to use transgenic pigs as organ donors for xenotransplantation by expressing human regulators of complement activation to prevent hyperacute rejection during organ transplantation (Cozzi and White, 1995). The development of disease resistant animals has also been tested in transgenic mice (e.g. Chen et al., 1988).

Fish are also an intensive research subject of transgenic studies. There are many ways of introducing a foreign gene into fish, including: microinjection (e.g. Zhu et al., 1985; Du et al., 1992), electroporation (Powers et al., 1992), sperm-mediated gene transfer (Khoo et al., 1992; Sin et al., 1993), gene bombardment or gene gun (Zelemin et al., 1991), liposome-mediated gene transfer (Szelei et al., 1994), and the direct injection of DNA into muscle tissue (Xu et al., 1999). The first transgenic fish report was published by Zhu et al. (1985) using a chimeric gene construct consisting of a mouse metallothionein gene promoter and a human growth hormone gene. Most of the early transgenic fish studies have concentrated on growth hormone gene transfer with an aim of generating fast growing "superfish". A majority of early attempts used heterologous growth hormone genes and promoters and failed to produce gigantic superfish (e.g. Chourrout et al., 1986; Penman et al., 1990; Brem et al., 1988; Gross et al., 1992). But enhanced growth of transgenic fish has been demonstrated in several fish species including Atlantic salmon, several species of Pacific salmons, and loach (e.g. Du et al., 1992; Delvin et al., 1994, 1995; Tsai et al., 1995).

The zebrafish, *Danio rerio*, is a new model organism for vertebrate developmental biology. As an experimental model, the zebrafish offers several major advantages such as easy availability of eggs and embryos, tissue clarity throughout embryogenesis, external development, short generation time and easy maintenance of both the adult and the young. Transgenic zebrafish have been used as an experimental tool in zebrafish developmental biology. However, despite the fact that the first transgenic zebrafish was reported a decade ago (Stuart et al., 1988), most transgenic zebrafish work conducted so far used heterologous gene promoters or viral gene promoters: e.g. viral promoters from SV40 (simian virus 40) and RSV (Rous sarcoma virus) (Stuart et al., 1988, 1990; Bayer and Campos-Ortega, 1992), a carp actin promoter (Liu et al., 1990), and mouse homeobox gene promoters (Westerfield et al., 1992). As a result, the expression pattern of a transgene in many cases is variable and unpredictable.

GFP (green fluorescent protein) was isolated from a jelly fish, *Aqueous victoria*. The wild type GFP emits green fluorescence at a wavelength of 508 nm upon stimulation with ultraviolet light (395 nm). The primary structure of GFP has been elucidated by cloning of its cDNA and genomic DNA (Prasher et al., 1992). A modified GFP, also called EGFP (Enhanced Green Fluorescent Protein) has been generated artificially and it contains mutations that allow the protein to emit a stronger green light and its coding sequence has also been optimized for higher expression in mammalian cells based on preferable human codons. As a result, EGFP fluorescence is about 40 times stronger than the wild type GFP in mammalian cells (Yang et al., 1996). GFP (including EGFP) has become a popular tool in cell biology and transgenic research. By fusing GFP with a tested protein, the GFP fusion protein can be used as an indicator of the subcellular location of the tested protein (Wang and Hazelrigg, 1994). By transformation of cells with a functional GFP gene, the GFP can be used as a marker to identify expressing cells (Chalfie et al., 1994). Thus, the GFP gene has become an increasingly popular reporter gene for transgenic research as GFP can be easily detected by a non-invasive approach.

The GFP gene (including EGFP gene) has also been introduced into zebrafish in several previous reports by using various gene promoters, including Xenopus elongation factor 1α enhancer-promoter (Amsterdam et al., 1995, 1996), rat myosin light-chain enhancer (Moss et al., 1996), zebrafish GATA-1 and GATA-3 promoters (Meng et al., 1997; Long et al., 1997), zebrafish α- and β-actin promoters (Higashijima et al., 1997), and tilapia insulin-like growth factor I promoter (Chen et al., 1998). All of these transgenic experiments aim at either developing a GFP transgenic system for gene expression analysis or at testing regulatory DNA elements in gene promoters.

SUMMARY OF INVENTION

It is a primary objective of the invention to clone fish gene promoters that are constitutive (ubiquitous), or that have tissue specificity such as skin specificity or muscle specificity or that are inducible by a chemical substance, and to use these promoters to develop effective gene constructs for production of transgenic fish.

It is another objective of the invention to develop fluorescent transgenic ornamental fish using these gene constructs. By applying different gene promoters, tissue-specific, inducible under different environmental conditions, or ubiquitous, to drive the GFP gene, GFP could be expressed in different tissues or ubiquitously. Thus, these transgenic fish may be skin fluorescent, muscle fluorescent, ubiquitously fluorescent, or inducibly fluorescent. These transgenic fish may be used for ornamental purposes, for monitoring environmental pollution, and for basic studies such as recapitulation of gene expression programs or monitoring cell lineage and cell migration. These transgenic fish may be used for cell transplantation and nuclear transplantation or fish cloning.

Other objectives, features and advantages of the present invention will become apparent from the detailed description which follows, or may be learned by practice of the invention.

Four zebrafish gene promoters of different characteristics were isolated and four chimeric gene constructs containing a zebrafish gene promoter and EGFP DNA were made: pCK-EGFP, pMCK-EGFP, pMLC2f-EGFP and pARP-EGFP. The first chimeric gene construct, pCK-EGFP, contains a 2.2 kbp polynucleotide comprising a zebrafish cytokeratin (CK) gene promoter which is specifically or predominantly expressed in skin epithelia. The second one, pMCK-EGFP, contains a 1.5 kbp polynucleotide comprising a muscle-specific promoter from a zebrafish muscle creatine kinase (MCK) gene and the gene is only expressed in the muscle tissue. The third construct, pMLC2f-EGFP contains a 2.2 kpb polynucleotide comprising a strong skeletal muscle-specific promoter from the fast skeletal muscle isoform of the myosin light chain 2 (MLC2f) gene and is expressed specifically or predominantly in skeletal muscle. The fourth chimeric gene construct, pARP-EGFP, contains a strong and ubiquitously expressed promoter from a zebrafish acidic ribosomal protein (ARP) gene. These four chimeric gene constructs have been introduced into zebrafish at the one cell stage by microinjection. In all cases, the GFP expression patterns were consistent with the specificities of the promoters. GFP was predominantly expressed in skin epithelia with pCK-EGFP, specifically expressed in muscles with pMCK-EGFP, specifically expressed in skeletal muscles with pMLC2f-EGFP and ubiquitously expressed in all tissues with pARP-EGFP.

These chimeric gene constructs are useful to generate green fluorescent transgenic fish. The GFP transgenic fish emit green fluorescence light under a blue or ultraviolet light and this feature makes the genetically engineered fish unique and attractive in the ornamental fish market. The fluorescent transgenic fish are also useful for the development of a biosensor system and as research models for embryonic studies such as cell lineage, cell migration, cell and nuclear transplantation etc.

BRIEF DESCRIPTION OF DRAWINGS

(FIG. 1A) A 28 hpf (hour postfertilization) embryo hybridized with a CK antisense riboprobe. (FIG. 1B) Enlargement of the mid-part of the embryo shown in FIG. 1A. (FIG. 1C) Cross-section of the embryo in FIG. 1A. (FIG. 1D) A 30 hpf embryo hybridized with an MCK antisense riboprobe. (FIG. 1E) Cross-section of the embryo in FIG. 1D. (FIG. 1F) A 28 hpf embryo hybridized with an ARP antisense riboprobe. (FIG. 1G) Cross-section of the embryo in FIG. 1F. Arrows indicate the planes for cross-sections and the box in panel A indicates the enlarged region shown in panel B. (FIG. 1H) Side view of a 22-hpf embryo hybridized with the MLC2f probe. (FIG. 1I) Transverse section through the trunk of a stained 24-hpf embryo. SC, spinal cord; N, notochord.

(FIG. 12A) High expression, GFP expression was detected in essentially 100% of the muscle fibers in the trunk. (FIG. 12B) Moderate expression, GFP expression was detected in several bundles of muscle fibers, usually in the mid-trunk region. (FIG. 12C) Low expression, GFP expression occurred in dispersed muscle fibers and the number of GFP positive fibers is usually less than 20 per embryo.

DETAILED DESCRIPTION

Figure 1A:
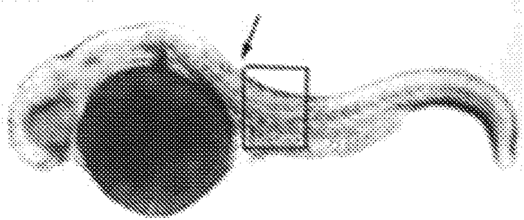
FIGS. 1A-1I are photographs showing expression of CK (FIGS. 1A-1C), MCK (FIGS. 1D-1E), ARP (FIGS. 1F-1G) and MLC2f (FIGS. 1H-1I) mRNAs in zebrafish embryos as revealed by whole mount in situ hybridization (detailed description of the procedure can be found in Thisse et al., 1993).

Gene Constructs.

To develop successful transgenic fish with a predictable pattern of transgene expression, the first step is to make a gene construct suitable for transgenic studies. The gene construct generally comprises three portions: a gene promoter, a structural gene and transcriptional termination signals. The gene promoter would determine where, when and under what conditions the structural gene is turned on. The structural gene contains protein coding portions that determine the protein to be synthesized and thus the biological function. The structural gene might also contain intron sequences which can affect mRNA stability or which might contain transcription regulatory elements. The transcription termination signals consist of two parts: a polyadenylation signal and a transcriptional termination signal after the polyadenylation signal. Both are important to terminate the transcription of the gene. Among the three portions, selection of a promoter is very important for successful transgenic study, and it is preferable to use a homologous promoter (homologous to the host fish) to ensure accurate gene activation in the transgenic host.

A promoter drives expression "predominantly" in a tissue if expression is at least 2-fold, preferably at least 5-fold higher in that tissue compared to a reference tissue. A promoter drives expression "specifically" in a tissue if the level of expression is at least 5-fold, preferably at least 10-fold higher, more preferably at least 50-fold higher in that tissue than in any other tissue.

Recombinant DNA Constructs.

Recombinant DNA constructs comprising one or more of the DNA or RNA sequences described herein and an additional DNA and/or RNA sequence are also included within the scope of this invention. These recombinant DNA constructs usually have sequences which do not occur in nature or exist in a form that does not occur in nature or exist in association with other materials that do not occur in nature. The DNA and/or RNA sequences described as constructs or in vectors above are "operably linked" with other DNA and/or RNA sequences. DNA regions are operably linked when they are functionally related to each other. For example, DNA for a presequence or secretory leader is operably linked to DNA for a polypeptide if it is expressed as part of a preprotein which participates in the secretion of the polypeptide; a promoter is operably linked to a coding sequence if it controls the transcription of the coding sequence; a ribosome binding site is operably linked to a coding sequence if it is positioned so as to permit translation. Generally, operably linked means contiguous (or in close proximity to) and, in the case of secretory leaders, contiguous and in reading phase.

The sequences of some of the DNAs, and the corresponding proteins encoded by the DNA, which are useful in the invention are set forth in the attached Sequence Listing.

The complete cytokeratin (CK) cDNA sequence is shown in SEQ ID NO:1, and its deduced amino acid sequence is shown in SEQ ID NO:2. The binding sites of the gene specific primers for promoter amplification, CK1 and CK2, are indicated. The extra nucleotides introduced into CK2 for generation of a restriction site are shown as a misc_feature in the primer sequence SEQ ID NO:11. A potential polyadenylation signal, AATAAA, is indicated in SEQ ID NO:1.

The complete muscle creatine kinase (MCK) cDNA sequence is shown in SEQ ID NO:3, and its deduced amino acid sequence is shown in SEQ ID NO:4. The binding sites of the gene specific primers for promoter amplification, MCK1 and MCK2, are indicated. The extra nucleotides introduced into MCK1 and MCK2 for generation of restriction sites are shown as a misc_feature in the primer sequences SEQ ID NOS:12 and 13, respectively. A potential polyadenylation signal, AATAAA, is indicated in SEQ ID NO:3.

The complete fast skeletal muscle isoform of myosin light chain 2 (MLC2f) cDNA sequence is shown in SEQ ID NO:20, and its deduced amino acid sequence is shown in SEQ ID NO:21. The binding sites of the gene-specific primers for promoter amplification, M1 and M2, are indicated. Two potential polyadenylation signals, AATAAA, are shown as a misc_feature in SEQ ID NO:20.

The complete acidic ribosomal protein P0 (ARP) cDNA sequence is shown in SEQ ID NO:5, and its deduced amino acid sequence is shown in SEQ ID NO:6. The binding sites of the gene specific primers for promoter amplification, ARP1 and ARP2, are indicated. The extra nucleotides introduced into ARP2 for generation of a restriction site are shown as a misc_feature in the primer sequence SEQ ID NO:15. A potential polyadenylation signal, AATAAA, is indicated in SEQ ID NO:5.

SEQ ID NO:7 shows the complete sequence of the CK promoter region. A putative TATA box is shown, and the 3' nucleotides identical to the 5' CK cDNA sequence are shown as a misc_feature. The binding site of the second gene specific primer, CK2, is shown. The introduced BamHI site is indicated as a misc_feature in the primer sequence SEQ ID NO:11.

SEQ ID NO:8 shows the complete sequence of the MCK promoter region. A putative TATA box is shown, and the 3' nucleotides identical to the 5' MCK cDNA sequence are shown as a misc_feature in SEQ ID NO:8. The binding site of the second gene specific primer, MCK2, is shown. The introduced BamHI site is indicated as a misc_feature in the primer sequence SEQ ID NO:13.

SEQ ID NO:22 shows the complete sequence of the MLC2f promoter region. A putative TATA box is shown, and the 3' nucleotides identical to the 5' MLC2f cDNA sequence are shown as a misc_feature. The binding site of the second gene-specific primer, M2, is shown. Potential muscle-specific cis-elements, E-boxes and MEF2 binding sites, are also shown. The proximal 1-kb region of the MLC2f promoter was recently published (Xu et al., 1999).

SEQ ID NO:9 shows the complete sequence of the ARP promoter region including the first intron. The first intron is shown, and the 3' nucleotides identical to the 5' ARP cDNA sequence are shown as misc_features. No typical TATA box is found. The binding site of the second gene specific primer, ARP2, is shown. The introduced BamHI site is indicated as a misc_feature in the primer sequence SEQ ID NO:15.

Specifically Exemplified Polypeptides/DNA.

The present invention contemplates use of DNA that codes for various polypeptides and other types of DNA to prepare the gene constructs of the present invention. DNA that codes for structural proteins, such as fluorescent peptides including GFP, EGFP, BFP, EBFP, YFP, EYFP, CFP, ECFP and enzymes (such as luciferase, β-galactosidase, chloramphenicol acetyltransferase, etc.), and hormones (such as growth hormone etc.), are useful in the present invention. More particularly, the DNA may code for polypeptides comprising the sequences exemplified in SEQ ID NOS:2, 4, 6 and 21. The present invention also contemplates use of particular DNA sequences, including regulatory sequences, such as promoter sequences shown in SEQ ID NOS: 7, 8, 9 and 22 or portions thereof effective as promoters. Finally, the present invention also contemplates the use of additional DNA sequences, described generally herein or described in the references cited herein, for various purposes.

Chimeric Genes.

The present invention also encompasses chimeric genes comprising a promoter described herein operatively linked to a heterologous gene. Thus, a chimeric gene can comprise a promoter of a zebrafish operatively linked to a zebrafish structural gene other than that normally found linked to the promoter in the genome. Alternatively, the promoter can be operatively linked to a gene that is exogenous to a zebrafish, as exemplified by the GFP and other genes specifically exemplified herein. Furthermore, a chimeric gene can comprise an exogenous promoter linked to any structural gene not normally linked to that promoter in the genome of an organism.

Variants of Specifically Exemplified Polypeptide.

DNA that codes for variants of the specifically exemplified polypeptides are also encompassed by the present invention. Possible variants include allelic variants and corresponding polypeptides from other organisms, particularly other organisms of the same species, genus or family. The variants may have substantially the same characteristics as the natural polypeptides. The variant polypeptide will possess the primary property of concern for the polypeptide. For example, the polypeptide will possess one or more or all of the primary physical (e.g., solubility) and/or biological (e.g., enzymatic activity, physiologic activity or fluorescence excitation or emission spectrum) properties of the reference polypeptide. DNA of the structural genes of the present invention will encode a protein that produces a fluorescent or chemiluminescent light under conditions appropriate to the particular polypeptide in one or more tissues of a fish. Preferred tissues for expression are skin, muscle, eye and bone.

Substitutions, Additions and Deletions.

As possible variants of the above specifically exemplified polypeptides, the polypeptide may have additional individual amino acids or amino acid sequences inserted into the polypeptide in the middle thereof and/or at the N-terminal and/or C-terminal ends thereof so long as the polypeptide possesses the desired physical and/or biological characteristics. Likewise, some of the amino acids or amino acid sequences may be deleted from the polypeptide so long as the polypeptide possesses the desired physical and/or biochemical characteristics. Amino acid substitutions may also be made in the sequences so long as the polypeptide possesses the desired physical and biochemical characteristics. DNA coding for these variants can be used to prepare gene constructs of the present invention.

Sequence Identity.

The variants of polypeptides or polynucleotides contemplated herein should possess more than 75% sequence identity (sometimes referred to as homology), preferably more than 85% identity, most preferably more than 95% identity, even more preferably more than 98% identity to the naturally occurring and/or specifically exemplified sequences or fragments thereof described herein. To determine this homology, two sequences are aligned so as to obtain a maximum match using gaps and inserts.

Two sequences are said to be "identical" if the sequence of residues is the same when aligned for maximum correspondence as described below. The term "complementary"

applies to nucleic acid sequences and is used herein to mean that the sequence is complementary to all or a portion of a reference polynucleotide sequence.

Optimal alignment of sequences for comparison can be conducted by the local homology algorithm of Smith and Waterman (1981), by the homology alignment method of Needleman and Wunsch (1970), by the search for similarity method of Pearson and Lippman (1988), or the like. Computer implementations of the above algorithms are known as part of the Genetics Computer Group (GCG) Wisconsin Genetics Software Package (GAP, BESTFIT, BLASTA, FASTA and TFASTA), 575 Science Drive, Madison, Wis. These programs are preferably run using default values for all parameters.

"Percentage of sequence identity" is determined by comparing two optimally aligned sequences over a comparison window, wherein the portion of the sequence in the comparison window may comprise additions or deletions (i.e. "gaps") as compared to the reference sequence for optimal alignment of the two sequences being compared. The percentage identity is calculated by determining the number of positions at which the identical residue occurs in both sequences to yield the number of matched positions, dividing the number of matched positions by the total number of positions in the window and multiplying the result by 100 to yield the percentage of sequence identity. Total identity is then determined as the average identity over all of the windows that cover the complete query sequence.

Fragments of Polypeptide.

Genes which code for fragments of the full length polypeptides such as proteolytic cleavage fragments which contain at least one, and preferably all, of the abovephysical and/or biological properties are also encompassed by the present invention.

DNA and RNA.

The invention encompasses DNA that codes for any one of the abovepolypeptides including, but not limited to, those shown in SEQ ID NOS:2, 4, 6 and 21 including fusion polypeptides, variants and fragments thereof. The sequence of certain particularly useful cDNAs which encode polypeptides are shown in SEQ ID NOS:1, 3, 5 and 20. The present invention also includes cDNA as well as genomic DNA containing or comprising the requisite nucleotide sequences as well as corresponding RNA and antisense sequences.

Cloned DNA within the scope of the invention also includes allelic variants of the specific sequences presented in the attached Sequence Listing. An "allelic variant" is a sequence that is a variant from that of the exemplified nucleotide sequence, but represents the same chromosomal locus in the organism. In addition to those which occur by normal genetic variation in a population and perhaps fixed in the population by standard breeding methods, allelic variants can be produced by genetic engineering methods. A preferred allelic variant is one that is found in a naturally occurring organism, including a laboratory strain. Allelic variants are either silent or expressed. A silent allele is one that does not affect the phenotype of the organism. An expressed allele results in a detectable change in the phenotype of the trait represented by the locus.

A nucleic acid sequence "encodes" or "codes for" a polypeptide if it directs the expression of the polypeptide referred to. The nucleic acid can be DNA or RNA. Unless otherwise specified, a nucleic acid sequence that encodes a polypeptide includes the transcribed strand, the hnRNA and the spliced RNA or the DNA representative of the mRNA.

An "antisense" nucleic acid is one that is complementary to all or part of a strand representative of mRNA, including untranslated portions thereof.

Degenerate Sequences.

In accordance with degeneracy of genetic code, it is possible to substitute at least one base of the base sequence of a gene by another kind of base without causing the amino acid sequence of the polypeptide produced from the gene to be changed. Hence, the DNA of the present invention may also have any base sequence that has been changed by substitution in accordance with degeneracy of genetic code.

DNA Modification.

The DNA is readily modified by substitution, deletion or insertion of nucleotides, thereby resulting in novel DNA sequences encoding the polypeptide or its derivatives. These modified sequences are used to produce mutant polypeptide and to directly express the polypeptide. Methods for saturating a particular DNA sequence with random mutations and also for making specific site-directed mutations are known in the art; see e.g. Sambrook et al. (1989).

Hybridizable Variants.

The DNA molecules useful in accordance with the present invention can comprise a nucleotide sequence selected from the group consisting of SEQ ID NOS.:1, 3, 5, 7-20 and 22-24 or can comprise a nucleotide sequence that hybridizes to a DNA molecule comprising the nucleotide sequence of SEQ ID NOS.:1, 3, 5 or 20 under salt and temperature conditions providing stringency at least as high as that equivalent to 5×SSC and 42° C. and that codes on expression for a polypeptide that has one or more or all of the abovephysical and/or biological properties. The present invention also includes polypeptides coded for by these hybridizable variants. The relationship of stringency to hybridization and wash conditions and other considerations of hybridization can be found in Chapters 11 and 12 of Sambrook et al (1989). The present invention also encompasses functional promoters which hybridize to SEQ ID NOS:7, 8, 9 or 22 under the above-described conditions. DNA molecules of the invention will preferably hybridize to reference sequences under more stringent conditions allowing the degree of mismatch represented by the degrees of sequence identity enumerated above. The present invention also encompasses functional primers or linker oligonucleotides set forth in SEQ ID NOS:10-19 and 23-24 or larger primers comprising these sequences, or sequences which hybridize with these sequences under the above-described conditions. The primers usually have a length of 10-50 nucleotides, preferably 15-35 nucleotides, more preferably 18-30 nucleotides.

Vectors.

The invention is further directed to a replicable vector containing cDNA that codes for the polypeptide and that is capable of expressing the polypeptide.

The present invention is also directed to a vector comprising a replicable vector and a DNA sequence corresponding to the above described gene inserted into said vector. The vector may be an integrating or nonvector depending on its intended use and is conveniently a plasmid.

Transformed Cells.

The invention further relates to a transformed cell or microorganism containing cDNA or a vector which codes for the polypeptide or a fragment or variant thereof and that is capable of expressing the polypeptide.

Expression Systems Using Vertebrate Cells.

Interest has been great in vertebrate cells, and propagation of vertebrate cells in culture (tissue culture) has become a routine procedure. Examples of vertebrate host cell lines useful in the present invention preferably include cells from any of the fish described herein. Expression vectors for such cells ordinarily include (if necessary) an origin of replication, a promoter located upstream from the gene to be expressed, along with a ribosome-binding site, RNA splice site (if introngenomic DNA is used or if an intron is necessary to optimize expression of a cDNA), a polyadenylation site, and a transcription termination sequence.

EXAMPLES

The following examples are provided by way of illustration only and not by way of limitation. Those of skill will readily recognize a variety of noncritical parameters which can be changed or modified to yield essentially similar results.

Example I: Isolation of Skin-Specific, Muscle-Specific and Ubiquitously Expressed Zebrafish cDNA Clones cDNA clones were isolated and sequenced as described by Gong et al. (1997). Basically, random cDNA clones were selected from zebrafish embryonic and adult cDNA libraries and each clone was partially sequenced by a single sequencing reaction. The partial sequences were then used to identify the sequenced clones for potential function and tissue specificity. Of the distinct clones identified by this approach, four of them were selected: for skin specificity (clone A39 encoding cytokeratin, CK), for muscle specificity (clone E146 encoding muscle creatine kinase, MCK), for skeletal muscle specificity (clone A113 encoding the fast skeletal muscle isoform of the myosin light chain 2, MLC2f) and for ubiquitous expression (clone A150 encoding acidic ribosomal protein P0, ARP), respectively.

The four cDNA clones were sequenced, and their complete cDNA sequences with deduced amino acid sequences are shown in SEQ ID NOS:1, 3, 5, and 20 respectively. A39 encodes a type II basic cytokeratin and its closest homolog in mammals is cytokeratin 8 (65-68% amino acid identity). E146 codes for the zebrafish MCK and its amino acid sequence shares ~87% identity with mammalian MCKs. A113 encodes the fast skeletal muscle isoform of the myosin light chain 2. The deduced amino acid sequence of this gene is highly homologous to other vertebrate fast skeletal muscle MLC2f proteins (over 80% amino acid identity). The amino acid sequence of zebrafish ARP deduced from the A150 clone is 87-89% identical to those of mammalian ARPs.

To demonstrate their expression patterns, whole mount in situ hybridization (Thisse et al., 1993) was performed for developing embryos and Northern blot analyses (Gong et al., 1992) were carried out for selected adult tissues and for developing embryos.

Figure 1B:
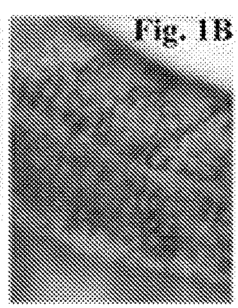
Figure 1C:
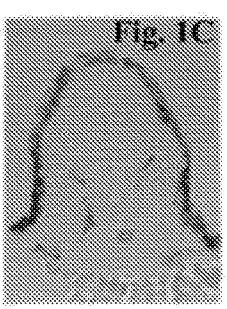

As indicated by whole mount in situ hybridization, cytokeratin mRNA was specifically expressed in the embryonic surface (FIGS. 1A-1C) and cross section of in situ hybridized embryos confirmed that the expression was only in skin epithelia (FIG. 1C). Ontogenetically, the cytokeratin mRNA appeared before 4 hours post-fertilization (hpf) and it is likely that the transcription of the cytokeratin gene starts at mid-blastula transition when the zygotic genome is activated. By in situ hybridization, a clear cytokeratin mRNA signal was detected in highly flattened cells of the superficial layer in blastula and the expression remained in the superficial layer which eventually developed into skin epithelia including the yolk sac. In adult tissues, cytokeratin mRNA was predominantly detected in the skin and also weakly in several other tissues including the eye, gill, intestine and muscle, but not in the liver and ovary (FIG. 2). Therefore, the cytokeratin mRNA is predominantly, if not specifically, expressed in skin cells.

Figure 1D:
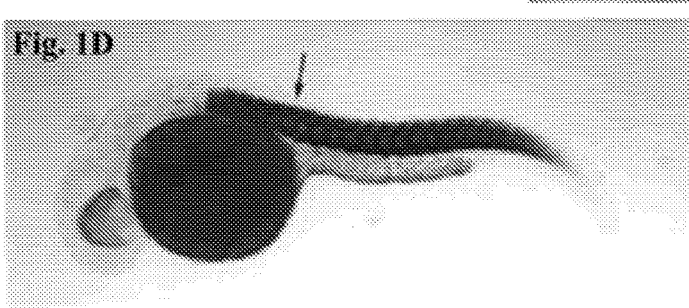
Figure 1E:
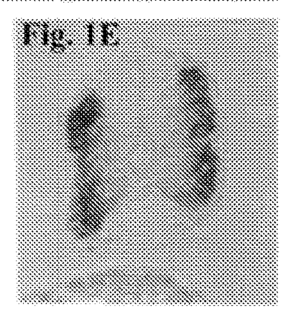

MCK mRNA was first detected in the first few anterior somites in 10 somite stage embryos (14 hpf) and at later stages the expression is specifically in skeletal muscle (FIG. 1D) and in heart (data not shown). When the stained embryos are cross-sectioned, the MCK mRNA signal was found exclusively in the trunk skeletal muscles (FIG. 1E). In adult tissues, MCK mRNA was detected exclusively in the skeletal muscle (FIG. 2).

Figure 1F:
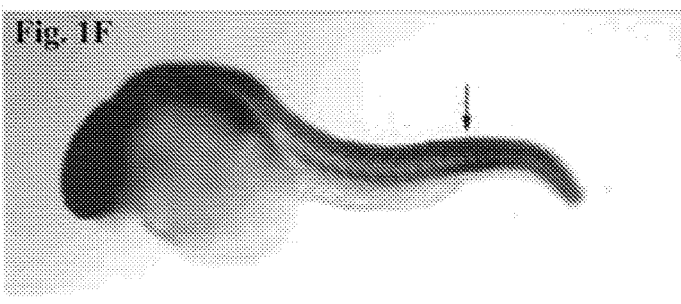
Figure 1G:
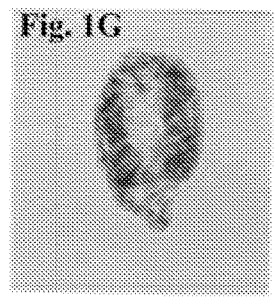
Figure 1H:
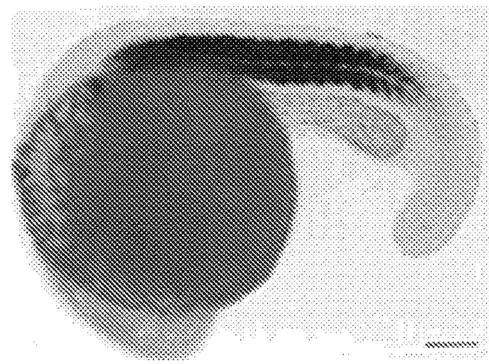
Figure 1I:
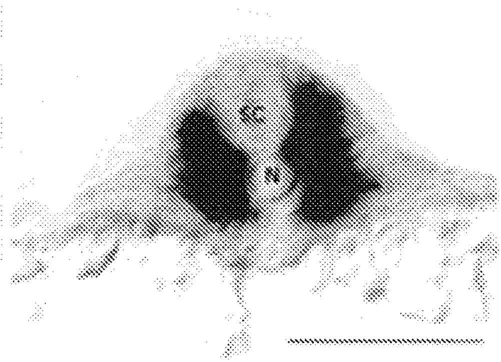
Figure 2A:
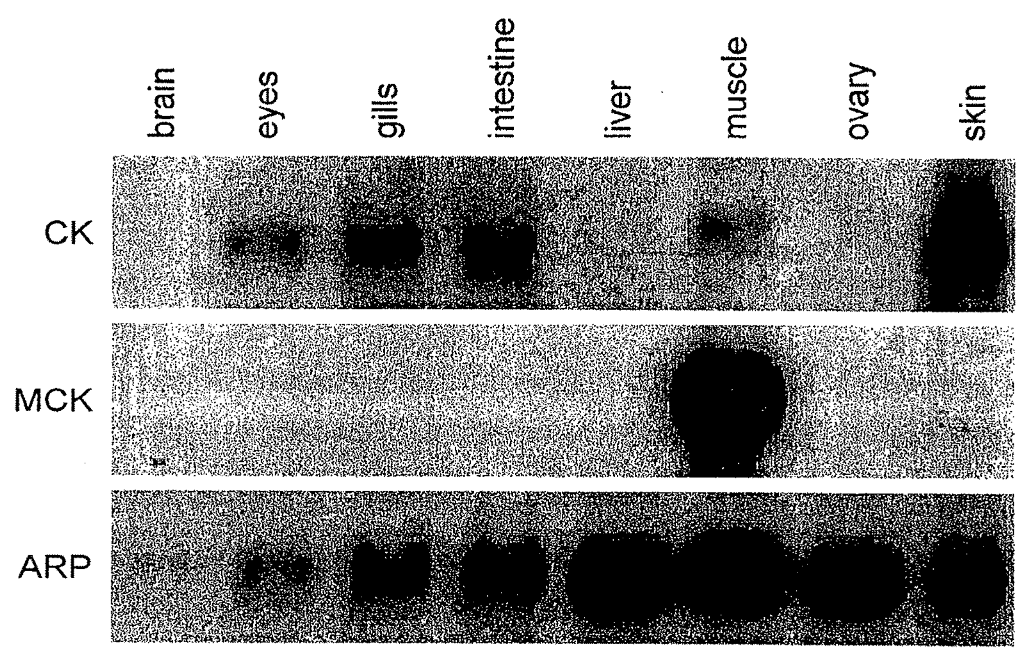
FIG. 2A is a digitized image showing distribution of CK, MCK and ARP mRNAs in adult tissues. Total RNAs were prepared from selected adult tissues as indicated at the top of each lane and analyzed by Northern blot hybridization (detailed description of the procedure can be found in Gong et al., 1992). Three identical blots were made from the same set of RNAs and hybridized with the CK, MCK and ARP probes, respectively.
Figure 2B:
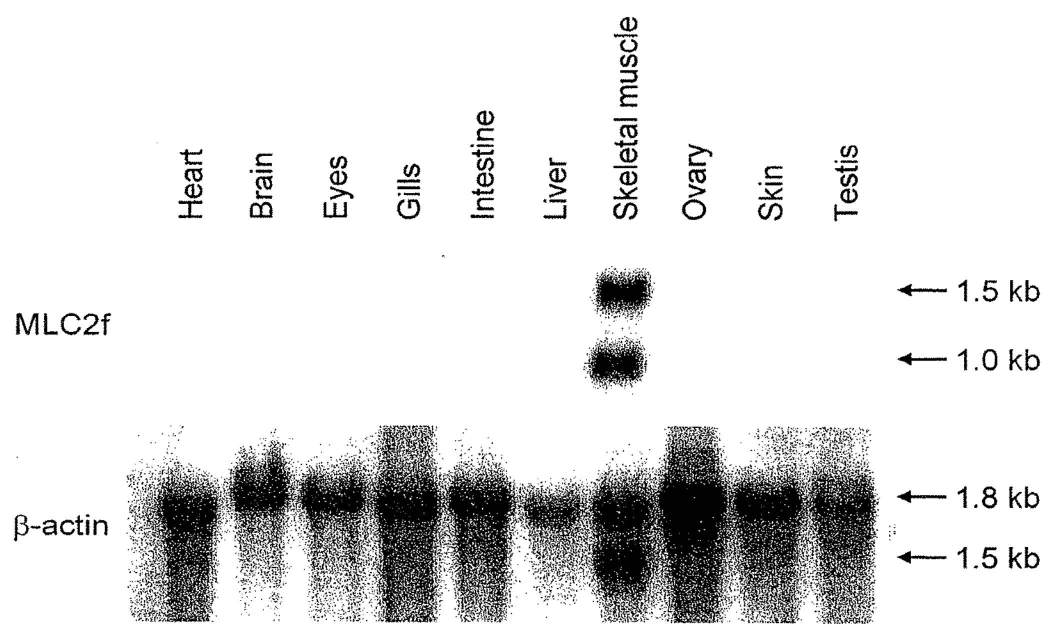
FIG. 2B is a digitized image showing distribution of MLC2f mRNA in adult tissues. Total RNAs were prepared from selected adult tissues as indicated at the top of each lane and analyzed by Northern blot hybridization (detailed description of the procedure can be found in Gong et al., 1992). Two identical blots were made from the same set of RNAs and hybridized with the MLC2f probe and a ubiquitously expressed R-actin probe, respectively.

MLC2f mRNA was specifically expressed in fast skeletal muscle in developing zebrafish embryos (FIGS. 1H-1I). To examine the tissue distribution of MLC2f mRNA, total RNAs were prepared from several adult tissues including heart, brain, eyes, gills, intestine, liver, skeletal muscle, ovary, skin, and testis. MLC2f mRNA was only detected in the skeletal muscle by Northern analysis; while α-actin mRNA was detected ubiquitously in the same set of RNAs, confirming the validity of the assay (FIG. 2B).

ARP mRNA was expressed ubiquitously and it is presumably a maternal mRNA since it is present in the ovary as well as in embryos at one cell stage. In in situ hybridization experiments, an intense hybridization signal was detected in most tissues. An example of a hybridized embryo at 28 hpf is shown in FIG. 1F. In adults, ARP mRNA was abundantly expressed in all tissues examined except for the brain where a relatively weak signal was detected (FIG. 2A). These observations confirmed that the ARP mRNA is expressed ubiquitously.

Example II: Isolation of Zebrafish Gene Promoters

Figure 3:
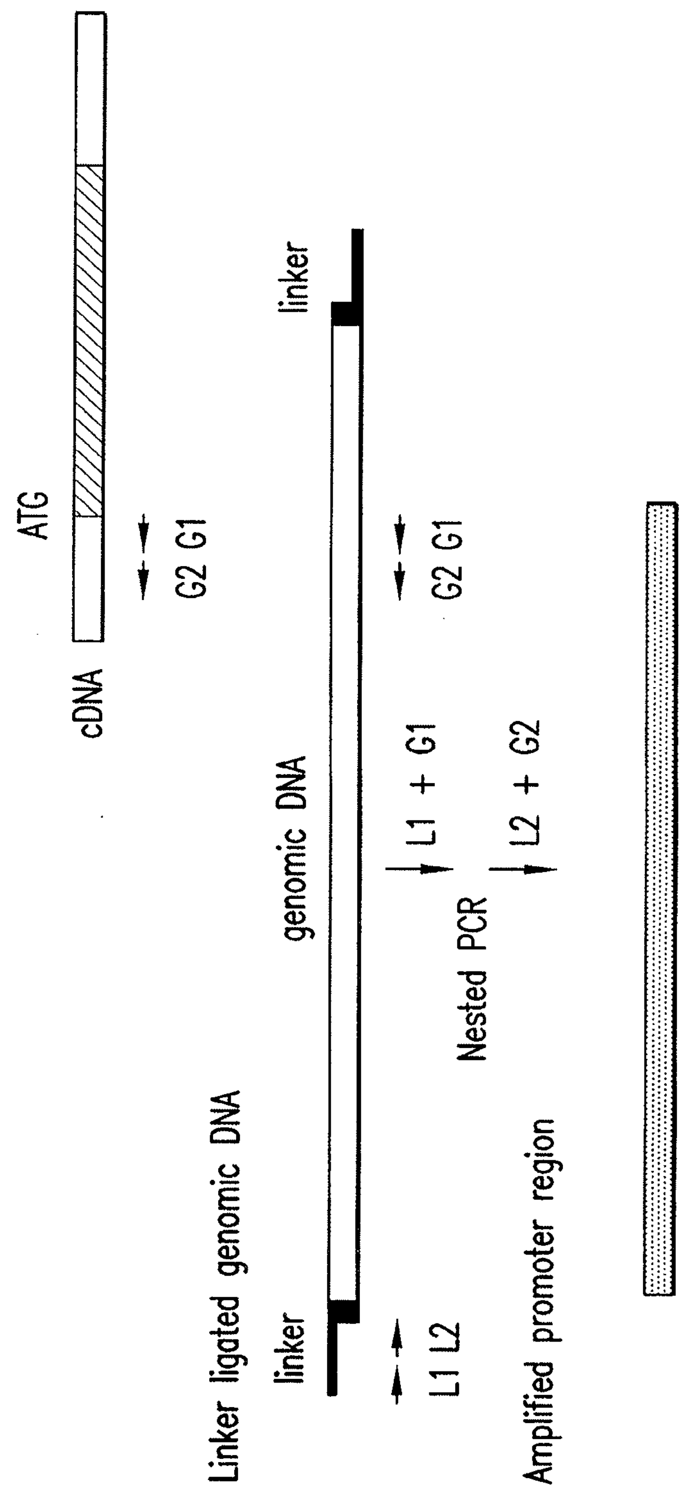
FIG. 3. is a schematic representation of the strategy of promoter cloning. Restriction enzyme digested genomic DNA was ligated with a short linker DNA which consists of Oligo 1 and Oligo 2. Nested PCR reactions were then performed: the first round PCR used linker specific primer L1 and gene specific primers G1, where G1 is CK1, MCK1, M1 or ARP1 in the described embodiments, and the second round linker specific primer L2 and gene specific primer G2, where G2 is CK2, MCK2, M2 or ARP2, respectively in the described embodiments.

Four zebrafish gene promoters were isolated by a linker-mediated PCR method as described by Liao et al., (1997) and as exemplified by the diagrams in FIG. 3. The whole procedure includes the following steps: 1) designing of gene specific primers; 2) isolation of zebrafish genomic DNA; 3) digestion of genomic DNA by a restriction enzyme; 4) ligation of a short linker DNA to the digested genomic DNA; 5) PCR amplification of the promoter region; and 6) DNA sequencing to confirm the cloned DNA fragment. The following is the detailed description of these steps.

1. Designing of gene specific primers. Gene specific PCR primers were designed based on the 5' end of the four cDNA sequences and the regions used for designing the primers are shown in SEQ ID NOS: 1, 3, 5 and 20.

The two cytokeratin gene specific primers are: CK1 (SEQ ID NO:10) CK2 (SEQ ID NO:11), where the first six nucleotides are for creation of an EcoRI site to facilitate cloning.

The two muscle creatine kinase gene specific primers are: MCK1 (SEQ ID NO:12), where the first five nucleotides are for creation of an EcoRI site to facilitate cloning.

MCK2 (SEQ ID NO:13), where the first three nucleotides are for creation of an EcoRI site to facilitate cloning.

The two fast skeletal muscle isoform of myosin light chain 2 gene specific primers are: M1 (SEQ ID NO:23) M2 (SEQ ID NO:24) The two acidic ribosomal protein P0 gene specific primers are: ARP1 (SEQ ID NO:14) ARP2 (SEQ ID NO:15), where the first six nucleotides are for creation of an EcoRI site to facilitate cloning.

2. Isolation of zebrafish genomic DNA. Genomic DNA was isolated from a single individual fish by a standard method (Sambrook et al., 1989). Generally, an adult fish was quickly frozen in liquid nitrogen and ground into powder.

The ground tissue was then transferred to an extraction buffer (10 mM Tris, pH 8, 0.1 M EDTA, 20 μg/ml RNase A and 0.5% SDS) and incubated at 37° C. for 1 hour. Proteinase K was added to a final concentration of 100 μg/ml and gently mixed until the mixture appeared viscous, followed by incubation at 50° C. for 3 hours with periodical swirling. The genomic DNA was gently extracted three times by phenol equilibrated with Tris-HCl (pH 8), precipitated by adding 0.1 volume of 3 M NaOAc and 2.5 volumes of ethanol, and collected by swirling on a glass rod, then rinsed in 70% ethanol.

3. Digestion of genomic DNA by a restriction enzyme. Genomic DNA was digested with the selected restriction enzymes. Generally, 500 units of restriction enzyme were used to digest 50 μg of genomic DNA overnight at the optimal enzyme reaction temperature (usually at 37° C.).

4. Ligation of a short linker DNA to the digested genomic DNA. The linker DNA was assembled by annealing equal moles of the two linker oligonucleotides, Oligo1 (SEQ ID NO:16) and Oligo 2 (SEQ ID NO:17). Oligo 2 was phosphorylated by T4 polynucleotide kinase prior to annealing. Restriction enzyme digested genomic DNA was filled-in or trimmed with T4 DNA polymerase, if necessary, and ligated with the linker DNA. Ligation was performed with 1 μg of digested genomic DNA and 0.5 μg of linker DNA in a 20 μl reaction containing 10 units of T4 DNA ligase at 4° C. overnight.

5. PCR amplification of promoter region. PCR was performed with Advantage Tth Polymerase Mix (Clontech). The first round of PCR was performed using a linker specific primer L1 (SEQ ID NO:18) and a gene specific primer G1 (CK1, MCK1, M1 or ARP1). Each reaction (50 μl) contains 5 μl of 10×Tth PCR reaction buffer (1×=15 mM KOAc, 40 mM Tris, pH 9.3), 2.2 μl of 25 mM Mg(OAc)2, 5 μl of 2 mM dNTP, 1 μl of L1 (0.2 μg/μl), 1 μl of G1 (0.2 μg/μl), 33.8 μl of H2O, and 1 μl (50 ng) of linker ligated genomic DNA and 1 μl of 50×Tth polymerase mix (Clontech). The cycling conditions were as follows: 94° C./1 min, 35 cycles of 94° C./30 sec and 68° C./6 min, and finally 68° C./8 min. After the primary round of PCR was completed, the products were diluted 100 fold. One μl of diluted PCR product was used as template for the second round of PCR (nested PCR) with a second linker specific primer L2 (SEQ ID NO:19) and a second gene specific primer G2 (CK2, MCK2, M2 or ARP2), as described for the primary PCR but with the following modification: 94° C./1 min, 25 cycles of 94° C./30 sec and 68° C./6 min, and finally 68° C./8 min. Both the primary and secondary PCR products were analyzed on a 1% agarose gel.

6. DNA sequencing to confirm the cloned DNA fragment. PCR products were purified from the agarose gel following electrophoresis and cloned into a TA vector, pT7Blue™ (Novogen). DNA sequencing was performed by dideoxynucleotide chain termination method using a T7 Sequencing Kit purchased from Pharmacia. Complete sequences of these promoter regions were obtained by automatic sequencing using a dRhodamine Terminator Cycle Sequencing Ready Reaction Kit (Perkin-Elmer) and an ABI 377 automatic sequencing machine.

The isolated cytokeratin DNA fragment comprising the gene promoter is 2.2 kb. In the 3' proximal region immediately upstream of a portion identical to the 3' part of the CK cDNA sequence, there is a putative TATA box perfectly matching to a consensus TATA box sequence. The 164 bp of the 3' region is identical to the 5' UTR (untranslated region) of the cytokeratin cDNA. Thus, the isolated fragment was indeed derived from the same gene as the cytokeratin cDNA clone (SEQ ID NO:7). Similarly, a 1.5 kb 5' flanking region was isolated from the muscle creatine kinase gene, a putative TATA box was also found in its 3' proximal region and the 3' region is identical to the 5' portion of the MCK cDNA clone (SEQ ID NO:8). For MLC2f, a 2 kb region was isolated from the fast skeletal muscle isoform of myosin light chain 2 gene and sequenced completely. The promoter sequence for MLC2f is shown in SEQ ID NO:22. The sequence immediately upstream of the gene specific primer M2 is identical to the 5' UTR of the MLC2f cDNA clone; thus, the amplified DNA fragments are indeed derived from the MLC2f gene. A perfect TATA box was found 30 nucleotides upstream of the transcription start site, which was defined by a primer extension experiment based on Sambrook et al. (1989). In the 2-kb region comprising the promoter, six E-boxes (CANNTG) and six potential MEF2 binding sites [C/T) TA(T/A)4TA(A/G)] were found and are indicated in SEQ ID NO:22. Both of these cis-element classes are important for muscle specific gene transcription (Schwarz et al., 1993; Olson et al., 1995). A 2.2 kb fragment was amplified for the ARP gene. By alignment of its sequence with the ARP cDNA clone, a 1.3 kb intron was found in the 5' UTR (SEQ ID NO:9). As a result, the isolated ARP promoter is within a DNA fragment about 0.8 kb long.

Example III: Generation of Green Fluorescent Transgenic Fish

Figure 4:
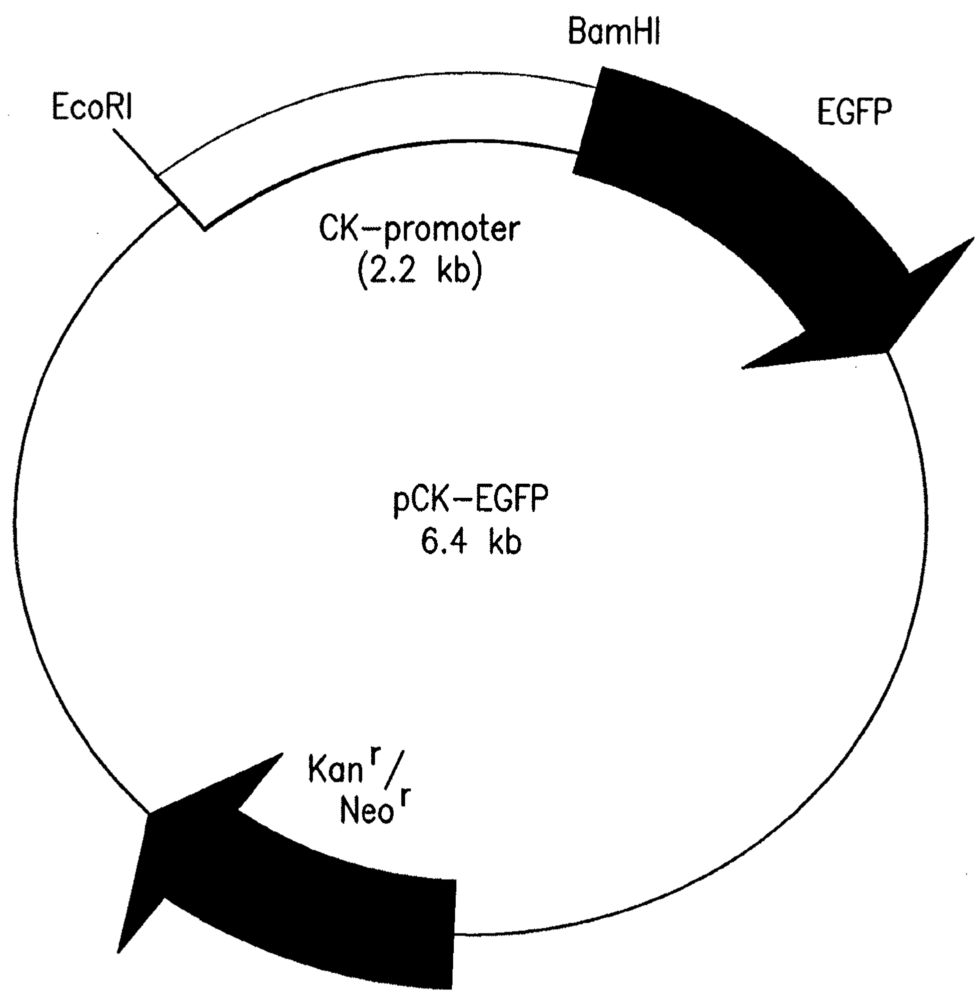
FIG. 4 is a schematic map of the chimeric gene construct, pCK-EGFP. The 2.2 kb zebrafish DNA fragment comprising the CK promoter region is inserted into pEGFP-1 (Clonetech) at the EcoRI and BamHI site as indicated. In the resulting chimeric DNA construct, the EGFP gene is under control of the zebrafish CK promoter. Also shown is the kanamycin/neomycin resistance gene ($Kan^r$/$Neo^r$) in the backbone of the original pEGFP-1 plasmid. The total length of the recombinant plasmid pCK-EGFP is 6.4 kb.
Figure 5:
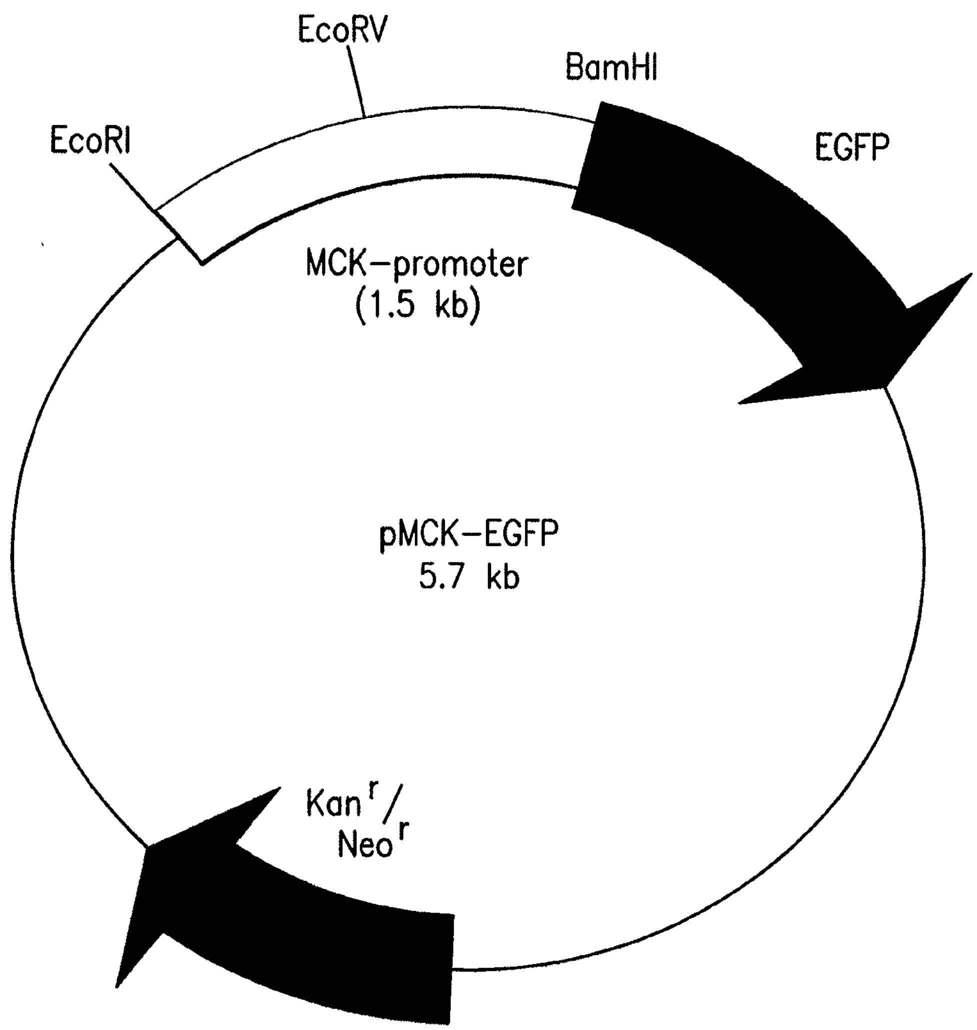
FIG. 5 is a schematic map of the chimeric gene construct, pMCK-EGFP. The 1.5 kb zebrafish DNA fragment comprising the MCK promoter region is inserted into pEGFP-1 (Clonetech) at the EcoRI and BamHI site as indicated. In the resulting chimeric DNA construct, the EGFP gene is under control of the zebrafish MCK promoter. Also shown is the kanamycin/neomycin resistance gene ($Kan^r/Neo^r$) in the backbone of the original pEGFP-1 plasmid. The total length of the recombinant plasmid pMCK-EGFP is 5.7 kb.
Figure 6:
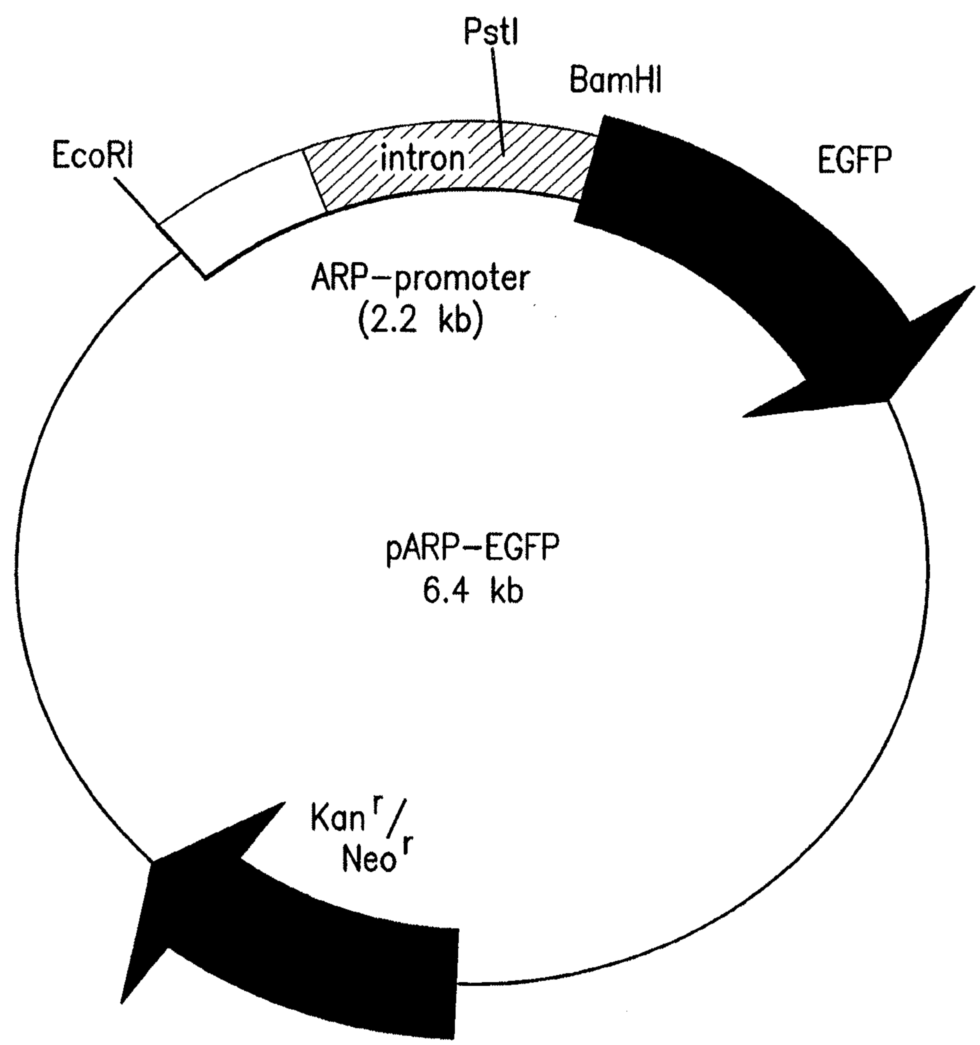
FIG. 6 is a schematic map of the chimeric gene construct, pARP-EGFP. The 2.2 kb zebrafish DNA fragment comprising the ARP promoter/1st intron region is inserted into pEGFP-1 (Clonetech) at the EcoRI and BamHI site as indicated. In the resulting chimeric DNA construct, the EGFP gene is under control of the zebrafish ARP promoter. Also shown is the kanamycin/neomycin resistance gene ($Kan^r/Neo^r$) in the backbone of the original pEGFP-1 plasmid. The total length of the recombinant plasmid pARP-EGFP is 6.4 kb.
Figure 7:
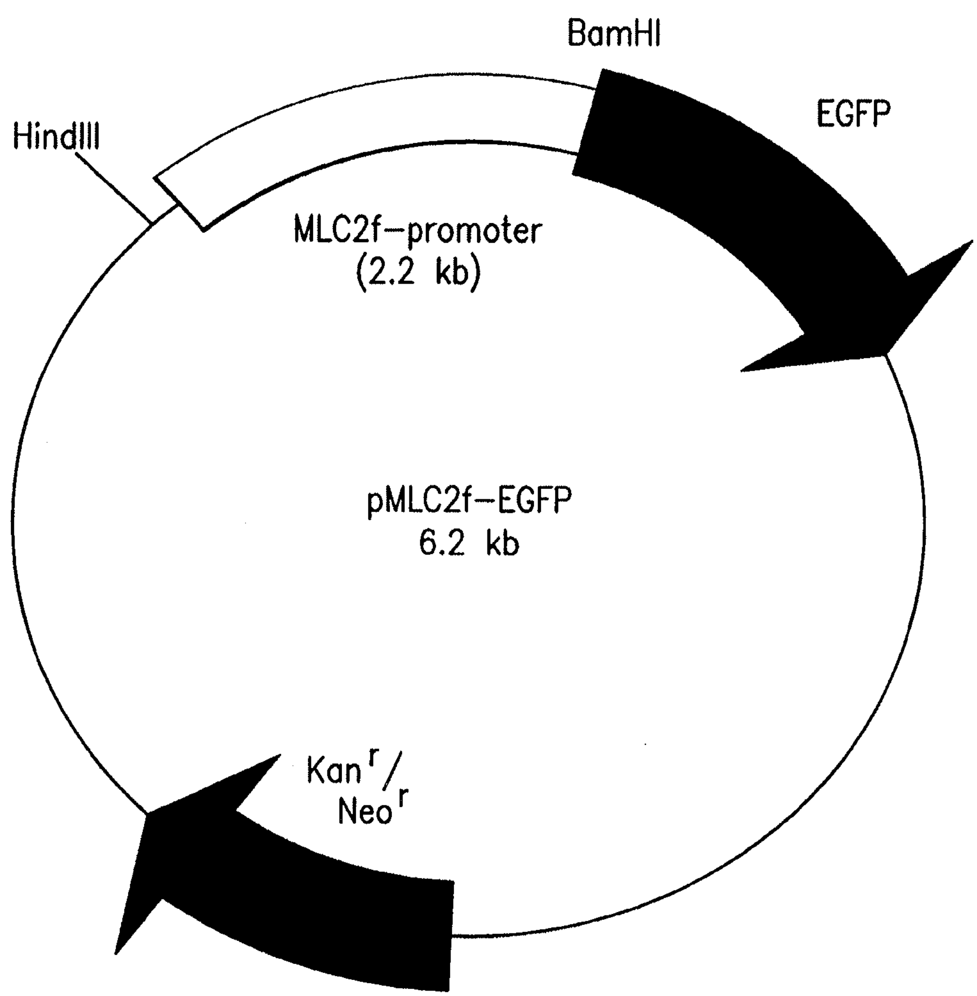
FIG. 7 is a schematic map of the chimeric gene construct, pMLC2f-EGFP. The 2.0 kb zebrafish DNA fragment comprising the MLC2f promoter region is inserted into pEGFP-1 (Clonetech) at the HindIII and BamHI site as indicated. In the resulting chimeric DNA construct, the EGFP gene is under control of the zebrafish MLC2f promoter. Also shown is the kanamycin/neomycin resistance gene ($Kan^r/Neo^r$) in the backbone of the original pEGFP-1 plasmid. The total length of the recombinant plasmid pMLC2f-EGFP is 6.2 kb.

The isolated zebrafish gene promoters were inserted into the plasmid pEGFP-1 (Clonetech), which contains an EGFP structural gene whose codons have been optimized according to preferable human codons. Three promoter fragments were inserted into pEGFP-1 at the EcoRI and BamHI site and the resulting recombinant plasmids were named pCK-EGFP (FIG. 4), pMCK-EGFP (FIG. 5), and pARP-EGFP, respectively (FIG. 6). The promoter fragment for the MLC2f gene was inserted into the Hind III and Bam HI sites of the plasmid pEGFP-1 and the resulting chimeric DNA construct, pMLC2f-EGFP, is diagramed in FIG. 7.

Linearized plasmid DNAs at a concentrations of 500 μg/ml (for pCK-EGFP and pMCK-EGFP) and 100 μg/ml (for pMLC2f-EGFP) in 0.1 M Tris-HCl (pH 7.6)/0.25% phenol red were injected into the cytoplasm of 1- or 2-cell stage embryos. Because of a high mortality rate, pARP-EGFP was injected at a lower concentration (50 μg/ml). Each embryo received 300-500 pl of DNA. The injected embryos were reared in autoclaved Holtfreter's solution (0.35% NaCl, 0.01% KCl and 0.01% CaCl2) supplemented with 1 μg/ml of methylene blue. Expression of GFP was observed and photographed under a ZEISS Axiovert 25 fluorescence microscope.

Figure 8:
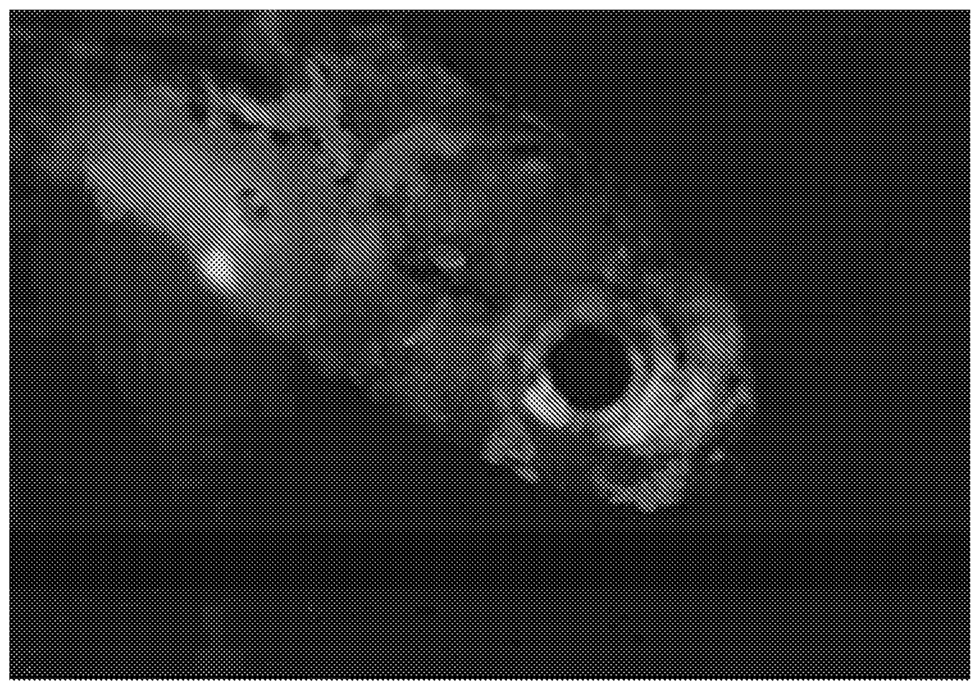
FIG. 8 is a photograph of a typical transgenic zebrafish fry (4 days old) with pCK-EGFP, which emits green fluorescence from skin epithelia under a blue light.

When zebrafish embryos received pCK-EGFP, GFP expression started about 4 hours after injection, which corresponds to the stage of ~30% epiboly. About 55% of the injected embryos expressed GFP at this stage. The early expression was always in the superficial layer of cells, mimicking endogenous expression of the CK gene as observed by in situ hybridization. At later stages, in all GFP-expressing fish, GFP was found predominantly in skin epithelia. A typical pCK-EGFP transgenic zebrafish fry at 4 days old is shown in FIG. 8.

Figure 9:
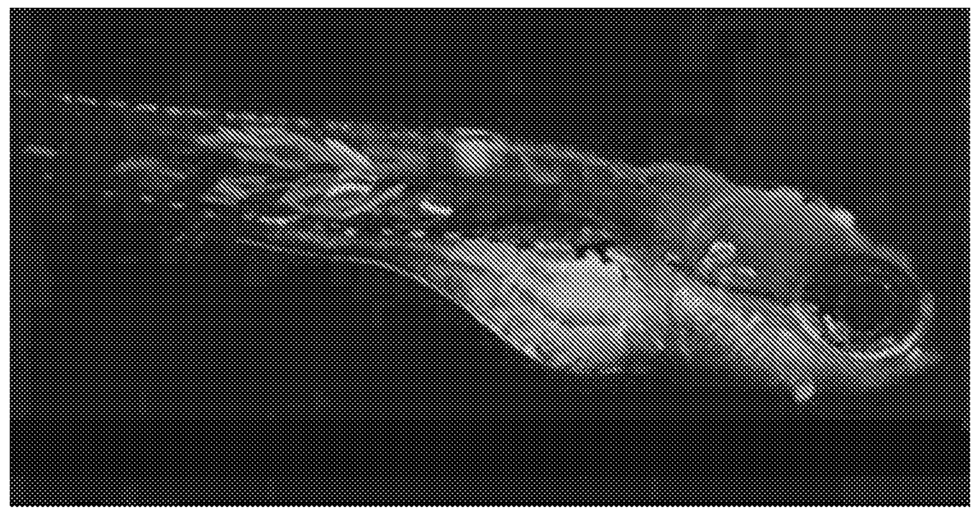
FIG. 9 is a photograph of a typical transgenic zebrafish fry (3 days old) with pMCK-EGFP, which emits green fluorescence from skeletal muscles under a blue light.

Under the MCK promoter, no GFP expression was observed in early embryos before muscle cells become differentiated. By 24 hpf, about 12% of surviving embryos expressed GFP strongly in muscle cells and these GFP-positive embryos remain GFP-positive after hatching. The GFP expression was always found in many bundles of muscle fibers, mainly in the mid-trunk region and no expression was ever found in other types of cells. A typical pMCK-EGFP transgenic zebrafish fry (3 days old) is shown in FIG. 9.

Figure 10:
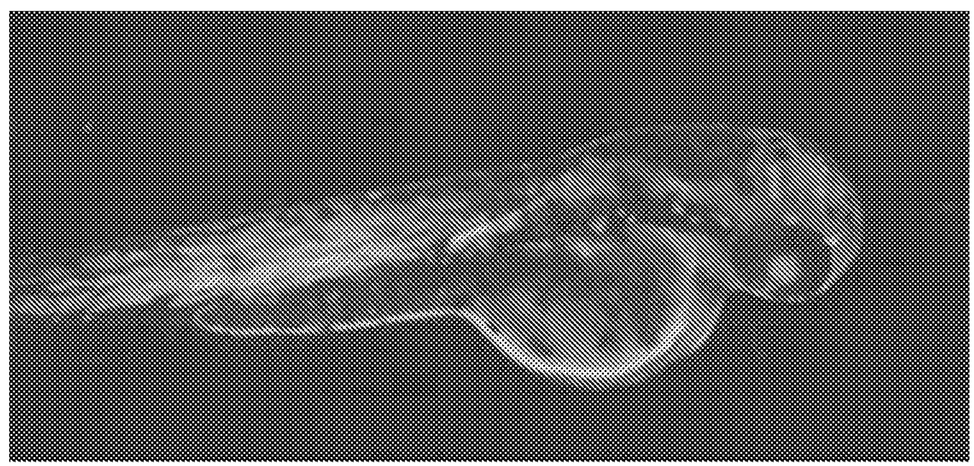
FIG. 10 is a photograph of a typical transgenic zebrafish fry (2 days old) with pARP-EGFP, which emits green fluorescence under a blue light from a variety of cell types such as skin epithelia, muscle cells, lens, neural tissues, notochord, circulating blood cells and yolk cells.

Expression of pARP-EGFP was first observed 4 hours after injection at the 30% epiboly stage. The timing of expression is similar to that of pCK-EGFP-injected embryos. However, unlike the pCK-EGFP transgenic embryos, the GFP expression under the ARP promoter occurred not only in the superficial layer of cells but also in deep layers of cells. In some batches of injected embryos, almost 100% of the injected embryos expressed initially. At later stages when some embryonic cells become overtly differentiated, it was found that the GFP expression occurred essentially in all different types of cells such as skin epithelia, muscle cells, lens, neural tissues, notochord, circulating blood cells and yolk cells (FIG. 10).

Under the MLC2f promoter, nearly 60% of the embryos expressed GFP. The earliest GFP expression started in trunk skeletal muscles about 19 hours after injection, which corresponds to the stage of 20-somite. Later, the GFP expression also occurred in head skeletal muscles including eye muscles, jaw muscles, gill muscles etc.

Figures 11A, 11B:
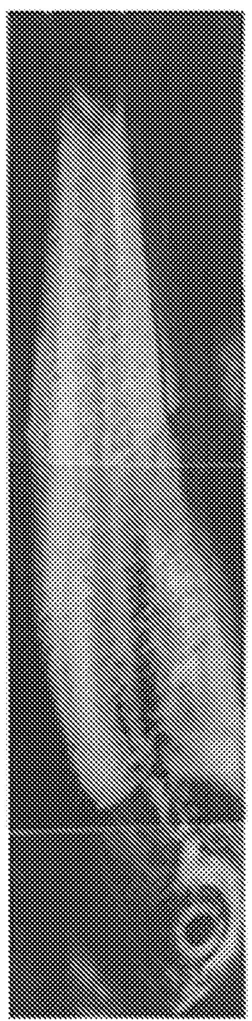
FIGS. 11A-11B. Photographs of a typical transgenic zebrafish founder with pMLC2f-EGFP (FIG. 11A) and an F1 stable transgenic offspring (FIG. 11B). Both pictures were taken under an ultraviolet light (365 nm). The green fluorescence can be better observed under a blue light with an optimal wavelength of 488 nm.

Transgenic founder zebrafish containing pMLC2f-EGFP emit a strong green fluorescent light under a blue or ultraviolet light (FIG. 11A). When the transgenic founders were crossed with wild-type fish, transgenic offspring were obtained that also displayed strong green fluorescence (FIG. 11B). The level of GFP expression is so high in the transgenic founders and offspring that green fluorescence can be observed when the fish are exposed to sunlight.

Figure 12A:
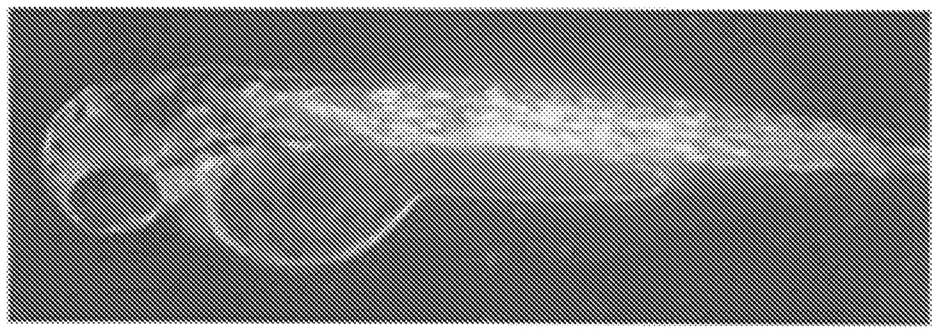
FIGS. 12A-12C. Examples of high, moderate and low expression of GFP in transiently transgenic embryos at 72 hpf.
Figure 12B:
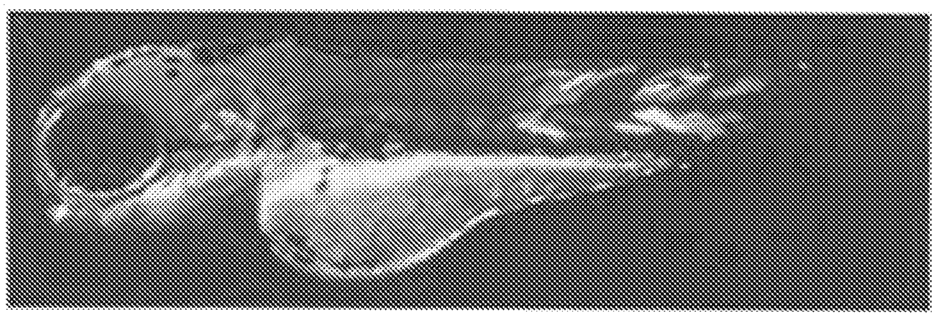
Figure 12C:
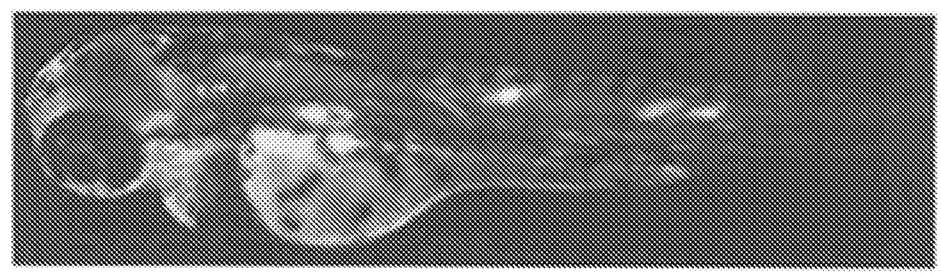

To identify the DNA elements conferring the strong promoter activity in skeletal muscles, deletion analysis of the 2-kb DNA fragment comprising the promoter was performed. Several deletion constructs, which contain 5" deletions of the MLC2f promoter upstream of the EGFP gene, were injected into the zebrafish embryos and the transient expression of GFP in early embryos (19-72 hpf) was compared. To facilitate the quantitative analysis of GFP expression, we define the level of expression as follows (FIGS. 12A-12C): Strong expression: GFP expression was detected in essentially 100% muscle fibers in the trunk.

Moderate expression: GFP expression was detected in several bundles of muscle fibers, usually in the mid-trunk region.

Weak expression: GFP expression occurred in dispersed muscle fibers and the number of GFP positive fibers is usually less than 20 per embryo.

Figure 13:
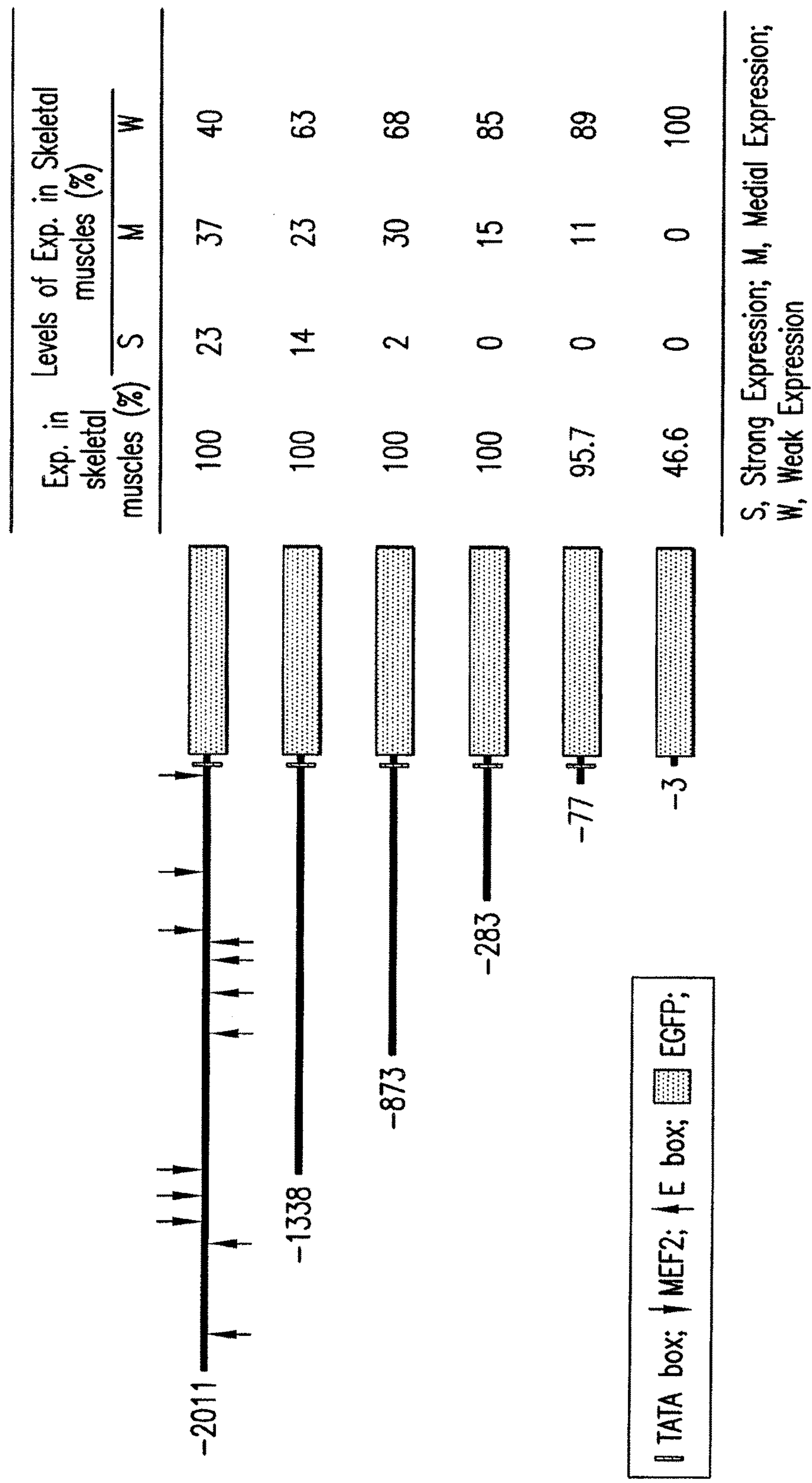
FIG. 13. Deletion analysis of the MLC2f promoter in transient transgenic zebrafish embryos. A series of 5" deletions of MLC2f-EGFP constructs containing 2011-bp (2-kb), 1338-bp, 873-bp, 283-bp, 77-bp and 3-bp of the MLC2f promoter were generated by unidirectional deletion using the double-stranded Nested Deletion Kit from Pharmacia based on the manufacturer's instructional manual. Each construct was injected into approximately 100 embryos and GFP expression was monitored in the first 72 hours of embryonic development. The level of GFP expression was classified based on the examples shown in FIGS. 12A-12C. Potential E-boxes and MEF2 binding sites, which are important for muscle-specific transcription (Schwarz et al., 1993; Olson et al., 1995), are indicated on the 2011-bp construct.

As shown in FIG. 13, deletion up to 283 bp maintained the GFP expression in skeletal muscles in 100% of the expressing embryos; however, the level of GFP expression from these deletion constructs varies greatly. Strong expression drops from 23% to 0% from the 2-kb (−2011 bp) promoter to the 283-bp promoter. Thus, only two constructs (2011 bp and 1338 bp) are capable of maintaining the high level of expression and the highest expression was obtained only with the 2-kb promoter, indicating the importance of the promoter region of 1338 bp to 2011 bp for conferring the highest promoter activity.

The expression of GFP using pMLC2f-EGFP is much higher than that obtained using the pMCK-EGFP that contains a 1.5 kb of zebrafish MCK promoter (Singapore Patent Application 9900811-2). By the same assay in transient transgenic zebrafish embryos, only about 12% of the embryos injected with pMCK-EGFP expressed GFP. Among the expressing embryos, no strong expression was observed, and 70% and 30% showed moderate and weak expression, respectively. In comparison, about 60% of the embryos injected with pMLC2f-EGFP expressed GFP and 23%, 37% and 40% showed strong, moderate and weak expression, respectively.

Example IV: Potential Applications of Fluorescent Transgenic Fish

The fluorescent transgenic fish have use as ornamental fish in the market. Stably transgenic lines can be developed by breeding a GFP transgenic individual with a wild type fish or another transgenic fish. By isolation of more zebrafish gene promoters, such as eye-specific, bone-specific, tail-specific etc., and/or by classical breeding of these transgenic zebrafish, more varieties of fluorescent transgenic zebrafish can be produced. Previously, we have reported isolation of over 200 distinct zebrafish cDNA clones homologous to known genes (Gong et al., 1997). These isolated clones code for proteins in a variety of tissues and some of them are inducible by heat-shock, heavy metals, or hormones such as estrogens. By using the method of PCR amplification using gene-specific primers designed from the nucleotide sequences of these cDNAs, and the linker-specific primers described herein, the promoters of the genes represented by the cDNAs of Gong et al. can be used in the present invention. Thus, hormone-inducible promoters, heavy-metal inducible promoters and the like from zebrafish can be isolated and used to make fluorescent zebrafish (or other fish species) that express a GFP or variant thereof, in response to the relevant compound.

Multiple color fluorescent fish may be generated by the same technique as blue fluorescent protein (BFP) gene, yellow fluorescent protein (YFP) gene and cyan fluorescent protein (CFP) gene are available from Clonetech. For example, a transgenic fish with GFP under an eye-specific promoter, BFP under a skin-specific promoter, and YFP under a muscle-specific promoter will show the following multiple fluorescent colors: green eyes, blue skin and yellow muscle. By recombining different tissue specific promoters and fluorescent protein genes, more varieties of transgenic fish of different fluorescent color patterns will be created. By expression of two or more different fluorescent proteins in the same tissue, an intermediate color may be created. For example, expression of both GFP and BFP under a skin-specific promoter, a dark-green skin color may be created.

By using a heavy metal—(such as cadmium, cobalt, chromium) inducible or hormone—(such as estrogen, androgen or other steroid hormone) inducible promoter, a biosensor system may be developed for monitoring environmental pollution and for evaluating water quality for human consumption and aquacultural uses. In such a biosensor system, the transgenic fish will glow with a green fluorescence (or other color depending on the fluorescence protein gene used) when pollutants such as heavy metals and estrogens (or their derivatives) reach a threshold concentration in an aquatic environment. Such a biosensor system has advantages over classical analytical methods because it is rapid, visualizable, and capable of identifying specific compounds directly in complex mixture found in an aquatic environment, and is portable or less instrument dependent. Moreover, the biosensor system also provides direct information on biotoxicity and it is biodegradable and regenerative.

Environmental monitoring of several substances can be accomplished by either creating one transgenic fish having genes encoding different colored fluorescent proteins driven by promoters responsive to each substance. Then the particular colors exhibited the fish in an environment can be observed. Alternatively, a number of fish can be transformed with individual vectors, then the fish can be combined into a population for monitoring an environment and the colors expressed by each fish observed.

In addition, the fluorescent transgenic fish should also be valuable in the market for scientific research tools because they can be used for embryonic studies such as tracing cell lineage and cell migration. Cells from transgenic fish expressing GFP can also be used as cellular and genetic markers in cell transplantation and nuclear transplantation experiments.

The chimeric gene constructs demonstrated successfully in zebrafish in the present invention should also be applicable to other fish species such as medaka, goldfish, carp including koi, loach, tilapia, glassfish, catfish, angel fish, discus, eel, tetra, goby, gourami, guppy, Xiphophorus (swordtail), hatchet fish, Molly fish, pangasius, etc. The promoters described herein can be used directly in these fish species. Alternatively, the homologous gene promoters from other fish species can be isolated by the method described in this invention. For example, the isolated and characterized zebrafish cDNA clones and promoters described in this invention can be used as molecular probes to screen for homologous promoters in other fish species by molecular hybridization or by PCR. Alternatively, one can first isolate the zebrafish cDNA and promoters based on the sequences presented in SEQ ID NOS:1, 3, 5, 7, 8, 9, 20 and 22 or using data from other sequences of cDNAs disclosed by Gong et al. 1997, by PCR and then use the zebrafish gene fragments to obtain homologous genes from other fish species by the methods mentioned above.

In addition, a strong muscle-specific promoter such as MLC2f is valuable to direct a gene to be expressed in muscle tissues for generation of other beneficial transgenic fish. For example, transgenic expression of a growth hormone gene under the muscle-specific promoter may stimulate somatic growth of transgenic fish. Such DNA can be introduced either by microinjection, electroporation, or sperm carrier to generate germ-line transgenic fish, or by direct injection of naked DNA into skeletal muscles (Xu et al., 1999) or into other tissues or cavities, or by a biolistic method (gene bombardment or gene gun) (Gomez-Chiarri et al., 1996).

The invention claimed is:

1. A transgenic fish comprising a chimeric gene comprising a zebrafish acidic ribosomal protein gene promoter operably linked to an exogenous gene, wherein said promoter comprises a nucleic acid sequence that is identical to the sequence of SEQ ID NO: 9, wherein the transgenic fish contains said promoter in germ cells and/or in somatic cells and is capable of breeding to produce viable and fertile transgenic progeny that express the exogenous gene.

2. The transgenic fish of claim 1, wherein the exogenous gene under the control of said promoter is a fluorescent protein gene.

3. The transgenic fish of claim 2, wherein said fish is an ornamental fish for the ornamental fish market.

4. The transgenic fish of claim 2, wherein said fish and progeny of said fish emits green fluorescence when the whole fish is exposed to a blue or ultraviolet light.

5. The transgenic fish of claim 1, further defined as a transgenic zebrafish, medaka, goldfish, carp, koi, loach, tilapia, glassfish, catfish, angel fish, discus, eel, tetra, goby, gourami, guppy, Xiphophorus, hatchet fish, Molly fish, or pangasius.

6. The transgenic fish of claim 5, further defined as a transgenic zebrafish, medaka, goldfish or carp.

7. The transgenic fish of claim 6, further defined as a transgenic zebrafish.

* * * * *